US007544362B1

(12) United States Patent
Yoo et al.

(10) Patent No.: US 7,544,362 B1
(45) Date of Patent: Jun. 9, 2009

(54) N PROTEIN MUTANTS OF PORCINE REPRODUCTIVE AND RESPIRATORY SYNDROME VIRUS

(75) Inventors: Dongwan Yoo, Guelph (CA); Changhee Lee, Guelph (CA); Jay Gregory Calvert, Otsego, MI (US); Siao-Kun Welch, Kalamazoo, MI (US)

(73) Assignee: Pfizer Inc., New York, NY (US)

( * ) Notice: Subject to any disclaimer, the term of this patent is extended or adjusted under 35 U.S.C. 154(b) by 100 days.

(21) Appl. No.: 11/359,334

(22) Filed: Feb. 22, 2006

Related U.S. Application Data

(60) Provisional application No. 60/656,523, filed on Feb. 25, 2005, provisional application No. 60/730,663, filed on Oct. 27, 2005.

(51) Int. Cl.
*A61K 39/00* (2006.01)
*C12N 7/00* (2006.01)
*C12N 7/04* (2006.01)

(52) U.S. Cl. .............. 424/204.1; 536/23.72; 435/235.1; 435/236; 514/44

(58) Field of Classification Search ........................ None
See application file for complete search history.

(56) References Cited

U.S. PATENT DOCUMENTS 6,268,199 B1* 7/2001 Meulenberg et al. ..... 435/235.1
2003/0049274 A1* 3/2003 Meulenberg et al. ..... 424/204.1

OTHER PUBLICATIONS

Yang et al (Archives of Virology 144:525-546, 1999).*
Shen et al (Archives of Virology 145:871-883, 2000)].*
NCBI AF184212, Sep. 28, 2000.*
Le Gall et al (Virus Research 54:9-21, 1998).*
Lee, C., Calvert, J. G., Welch, S.-K. W., and Yoo, D. (2005). A DNA-launched reverse genetics system for porcine reproductive and respiratory syndrome virus reveals that homodimerization of the nucleocapsid protein is essential for virus infectivity. Virology 331, 47-62.
Rowland, R. R., Kervin, R., Kuckleburg, C., Sperlich, A., and Benfield, D. A. (1999). The localization of porcine reproductive and respiratory syndrome virus nucleocapsid protein to the nucleolus of infected cells and identification of a potential nucleolar localization signal, Virology 316, 135-145.
Rowland, R. R. R., Schneider, P., Fang, Y., Wootton, S., Yoo, D., and Benfield, D. A. (2003). Peptide domains involved in the localization of the porcine reproductive and respiratory syndrome virus nucleocapsid protein to the nucleolus. Virology 316(1), 135-145 (Abstract).
Rowland, R. R. R., and Yoo, D. (2003). Nucleolar-cytoplasmic shuttling of PRRSV nucleocapsid protein: a simple case of molecular mimicry or the complex regulation by nuclear import, nucleolar localization and nuclear export signal sequences. Virus Research 95, 23-33.
Wootton, S. K., Rowland, R. R. R., and Yoo, D. (2002). Phosphorylation of the porcine reproductive and respiratory syndrome virus nucleocapsid protein. Journal of Virology 76 (20), 10569-10576.

(Continued)

*Primary Examiner*—Mary E Mosher
(74) *Attorney, Agent, or Firm*—Lorraine B. Ling; Bruce Weintraub; E. Victor Donahue

(57) ABSTRACT

The present invention provides a genetically modified PRRS virus, methods to make it and related polypeptides, polynucleotides and various components. Vaccines comprising the genetically modified virus and polynucleotides are also provided.

19 Claims, 6 Drawing Sheets

OTHER PUBLICATIONS

Wootton, S. K., and Yoo, D. (2003). Homo-oligomerization of the porcine reproductive and respiratory syndrome virus nucleocapsid protein and the role of disulfide linkages. Journal of Virology 77(8), 4546-4557.

Yoo, D., Wootton, S. K., Li, G., Song, C., and Rowland, R. R. (2003). Colocalization and interaction of the porcine arterivirus nucleocapsid protein with the small nucleolar RNA-associated protein fibrillarin. Journal of Virology 77(22), 12173-12183.

Yoo, D., Welch, S.-K. W., Lee, C., and Calvert, J. G. (2004). Infectious clones of porcine reproductive and respiratory syndrome virus and their potential as vaccine vectors. Veterinary Immunology and Immunopathology 102, 143-154.

* cited by examiner

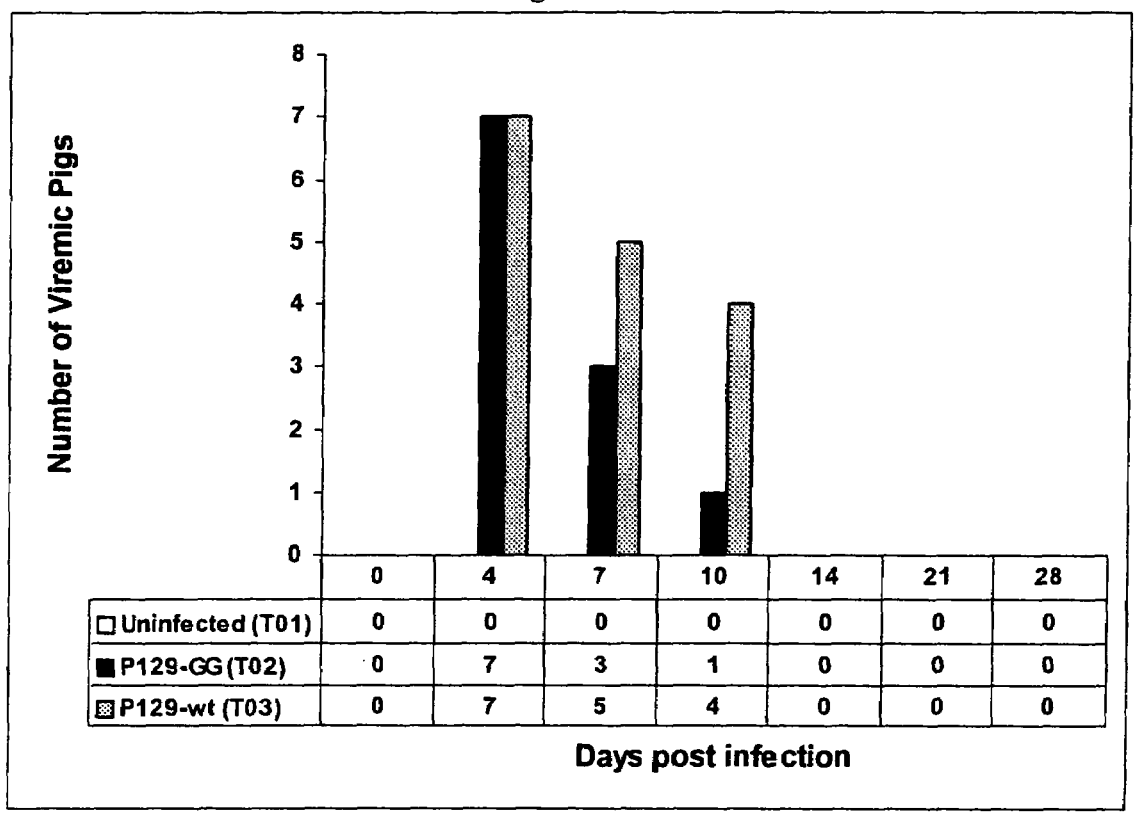

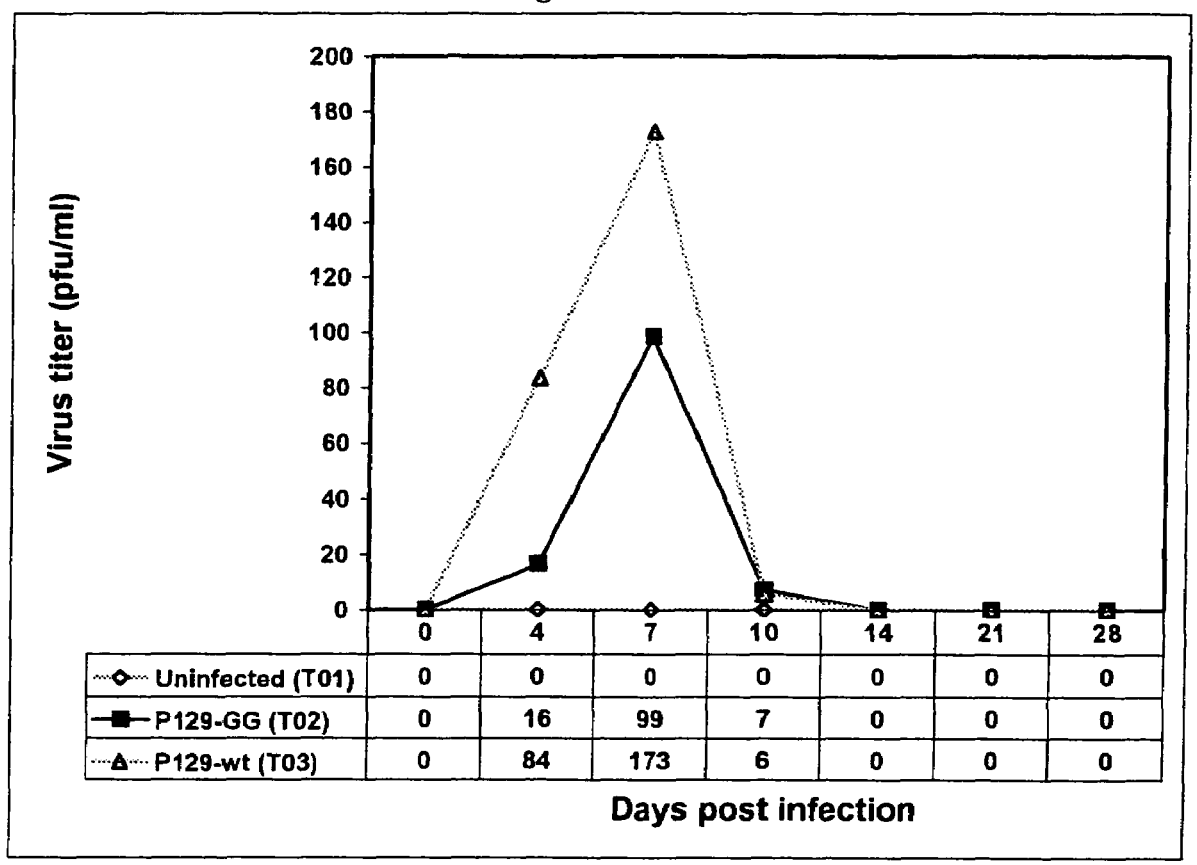

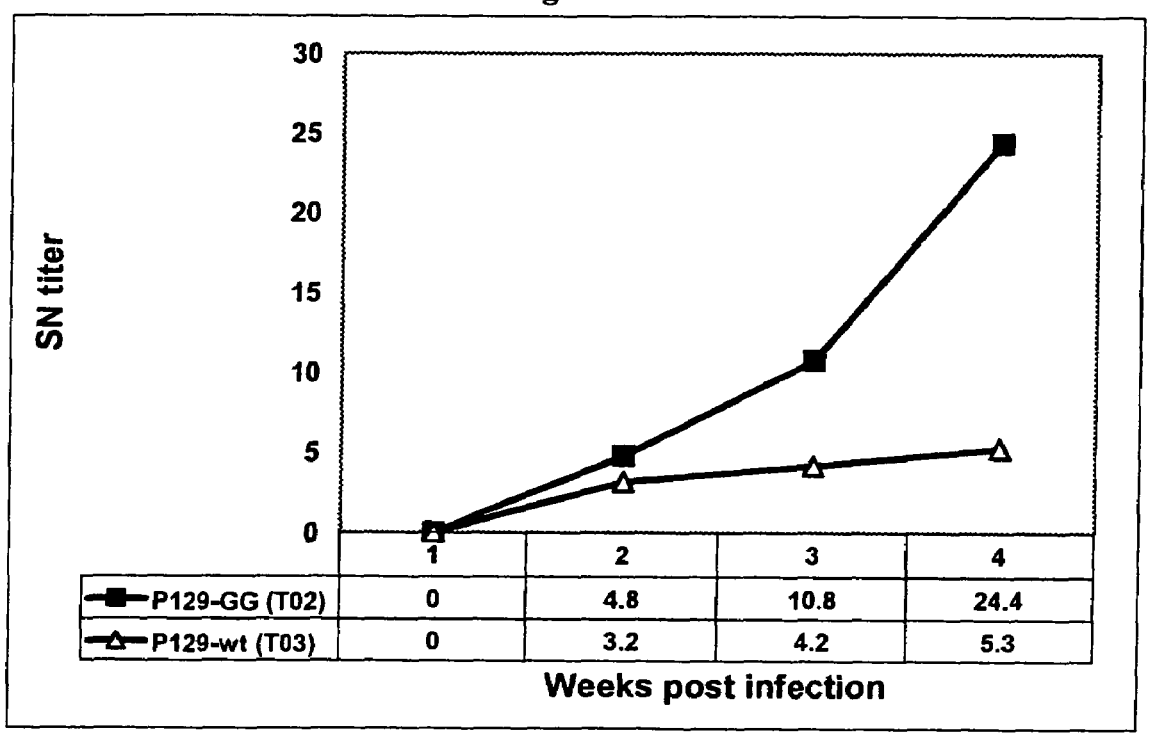

US 7,544,362 B1

N PROTEIN MUTANTS OF PORCINE REPRODUCTIVE AND RESPIRATORY SYNDROME VIRUS

CROSS-REFERENCE TO RELATED APPLICATIONS

This application claims the benefit of U.S. Provisional Patent Application Nos. 60/656,523 and 60/730,663 respectively filed on Feb. 25, 2005 and Oct. 27, 2005, which are incorporated herein in their entirety.

FIELD OF THE INVENTION

The present invention provides a genetically modified PRRS virus and polynucleotides that encode it. Vaccines comprising the genetically modified virus and polynucleotides are also provided.

BACKGROUND OF THE INVENTION

Porcine reproductive and respiratory syndrome (PRRS) is characterized by abortions, stillbirths, and other reproductive problems in sows and gilts, as well as respiratory disease in young pigs. The causative agent is the PRRS virus, a member of the family Arteriviridae and the order Nidovirales. Two distinct genotypes of the virus emerged nearly simultaneously in North America and in Europe in the late 1980's. PRRS virus is now endemic in nearly all swine producing countries, and is considered one of the most economically important diseases affecting the global pork industry.

Currently, commercial vaccines against PRRS include modified live and killed (inactivated) vaccines. Killed vaccines have been criticized for failing to induce robust immunity against heterologous strains of PRRS virus. Modified live vaccines are attenuated by serial passage in cell culture until virulence is lost. Modified live vaccines elicit broader protection than killed vaccines, but can suffer from a number of safety concerns including residual virulence, spread to non-vaccinated pigs, and genetic reversion to virulence. Because of antigenic changes that take place during the attenuation process, such vaccines can also lose some ability to protect against virulent field strains of PRRS virus. There is a pressing need therefore for new and improved modified live vaccines to protect against PRRS.

BRIEF DESCRIPTION OF THE SEQUENCES

Figure 1:
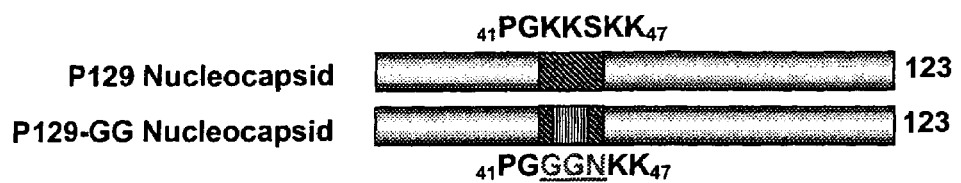
FIG. 1. (A) Drawing showing position and sequence of the NLS mutation within the P129 nucleocapsid protein. (B) Photomicrographs of mock infected, P129 infected, and P129-GG infected MARK-145 cells. Upper row shows typical plaques using phase contrast microscopy, while lower row shows fluorescent antibody staining of infected foci using FITC-conjugated monoclonal antibody SDOW17. Note the absence of nucleocapsid staining in the nuclei and nucleoli of cells infected with P129-GG.
Figure 1:
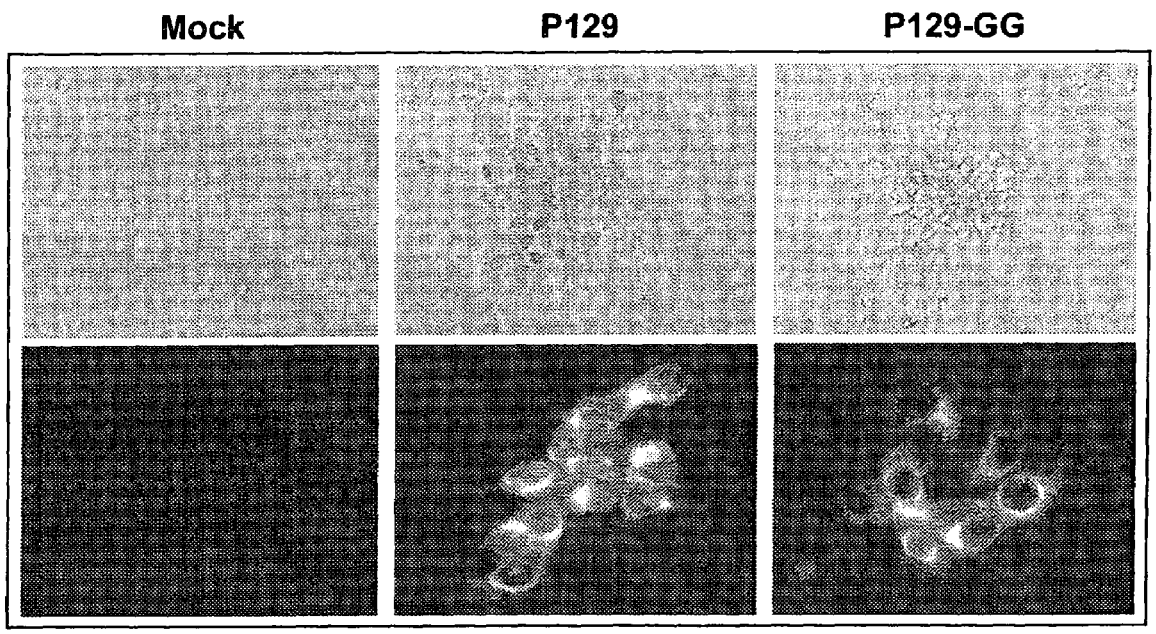

SEQ ID NO: 1 N protein residues 41-47 of the North American PRRSV isolate VR2332

SEQ ID NO: 2 VR2332NoLS region sequence

SEQ ID NO: 3 Lelystad NoLS region sequence

SEQ ID NO: 4 The NES region of the VR2332 isolate

SEQ ID NO: 5 The NES region of the Lelystad isolate

SEQ ID NO: 6 Amino acid sequence of N protein from P129 isolate

SEQ ID NO: 7 Nucleotide sequence of ORF 7 (encodes the N protein) from P129 isolate SEQ ID NO: 8 Primer P SHUTTLE FWD SEQ ID NO: 9 Primer P-SHUTTLE-REV SEQ ID NO: 10 Mutagenic primer KK43/44GG-Fwd SEQ ID NO: 11 Mutagenic primer KK43/44GG-REV SEQ ID NO: 12 Table 8 deletion mutants. Amino acid sequence of NLS2 region of wt P129:

SEQ ID NO: 13 Table 8 deletion mutants. Nucleotide sequence of NLS2 region of wt P129

SEQ ID NO: 14 Table 8 deletion mutants. Amino acid sequence of NLS2 region of P129-GG:

SEQ ID NO: 15 Table 8 deletion mutants. Nucleotide sequence of NLS2 region of

SEQ ID NO: 16 Table 8 deletion mutants. Amino acid sequence of NLS2 region of P129-d43/44:

SEQ ID NO: 17 Table 8 deletion mutants. Nucleotide sequence of NLS2 region of P129-d43/44:

SEQ ID NO: 18 Table 8 deletion mutants. Amino acid sequence of NLS2 region of P129-d43/44/46:

SEQ ID NO: 19 Table 8 deletion mutants. Nucleotide sequence of NLS2 region of P129-d43/44/46:

SEQ ID NO: 20 Table 8 deletion mutants. Amino acid sequence of NLS2 region of P129-d44/46/47:

SEQ ID NO: 21 Table 8 deletion mutants. Nucleotide sequence of NLS2 region of P129-d44/46/47:

SEQ ID NO: 22 Table 8 deletion mutants. Amino acid sequence of NLS2 region of P129-d46/47/48:

SEQ ID NO: 23 Table 8 deletion mutants. Nucleotide sequence of NLS2 region of P129-d46/47/48

SEQ ID NO: 24 P129-d43/44F

SEQ ID NO: 25 P129-d43/44/46F

SEQ ID NO: 26 P129-d44/46/47F

SEQ ID NO: 27 P129-d46/47/48F

SEQ ID NO: 28 P129-d43/44R

SEQ ID NO: 29 P129-d43/44/46R

SEQ ID NO: 30 P129-d44/46/47R

SEQ ID NO: 31 P129-d46/47/48R

REFERENCES CITED

Doan, D. N. P., and Dokland, T. (2003). Structure of the nucleocapsid protein of porcine reproductive and respiratory syndrome virus. Structure 11(11), 1445-1451. Lee, C., Calvert, J. G., Welch, S.-K. W., and Yoo, D. (2005). A DNA-launched reverse genetics system for porcine reproductive and respiratory syndrome virus reveals that homodimerization of the nucleocapsid protein is essential for virus infectivity. Virology 331, 47-62.

Rowland, R. R., Kervin, R., Kuckleburg, C., Sperlich, A., and Benfield, D. A. (1999). The localization of porcine reproductive and respiratory syndrome virus nucleocapsid protein to the nucleolus of infected cells and identification of a potential nucleolar localization signal sequence. Virus Research 64(1), 1-12.

Rowland, R. R. R., Schneider, P., Fang, Y., Wootton, S., Yoo, D., and Benfield, D. A. (2003). Peptide domains involved in the localization of the porcine reproductive and respiratory syndrome virus nucleocapsid protein to the nucleolus. Virology 316(1), 135-145.

Rowland, R. R. R., and Yoo, D. (2003). Nucleolar-cytoplasmic shuttling of PRRSV nucleocapsid protein: a simple case of molecular mimicry or the complex regulation by nuclear import, nucleolar localization and nuclear export signal sequences. Virus Research 95(1-2), 23-33.

Wootton, S. K., Rowland, R. R. R., and Yoo, D. (2002). Phosphorylation of the porcine reproductive and respiratory syndrome virus nucleocapsid protein. Journal of Virology 76(20), 10569-10576.

Wootton, S. K., and Yoo, D. (2003). Homo-oligomerization of the porcine reproductive and respiratory syndrome virus nucleocapsid protein and the role of disulfide linkages. Journal of Virology 77(8), 4546-4557.

Yoo, D., Wootton, S. K., Li, G., Song, C., and Rowland, R. R. (2003). Colocalization and interaction of the porcine arterivirus nucleocapsid protein with the small nucleolar RNA-associated protein fibrillarin. Journal of Virology 77(22), 12173-12183.

Yoo, D., Welch, S.-K. W., Lee, C., and Calvert, J. G. (2004). Infectious clones of porcine reproductive and respiratory syndrome virus and their potential as vaccine vectors. Veterinary Immunology and Immunopathology 102, 143-154.

SUMMARY OF THE INVENTION

The invention provides a genetically modified PRRS virus which has been modified within the NLS-2 region, NoLS region, and/or the NES region of the nucleocapsid (N) protein such that the resultant PRRS virus is attenuated. The subject invention further provides an infectious RNA molecule encoding the genetically modified virus and an isolated polynucleotide molecule comprising a DNA sequence encoding the infectious RNA molecule recited above.

The invention also provides a biologically pure culture of the viruses recited (i.e substantially free of other viruses) and it describes a viral vector comprising a DNA sequence encoding an infectious RNA molecule encoding a genetically modified PRRS virus as recited above.

The subject invention further provides a transfected host cell comprising any of the forgoing viruses, infectious RNA molecules, isolated polynucleotides or viral vectors recited above.

The subject invention further provides a vaccine for protecting a porcine animal from infection by a PRRS virus, which vaccine comprises a genetically modified PRRS virus as recited above; an infectious RNA molecule as recited above encoding the genetically modified PRRS virus; an isolated polynucleotide molecule recited above, (optionally in the form of a plasmid), encoding the genetically modified PRRS virus; or the above-recited viral vector encoding the genetically modified PRRS virus; in an amount effective to produce immunoprotection against infection by a PRRS virus; and a carrier acceptable for veterinary use.

The invention further provides for reversion-resistant mutations of NLS-2. Preferred embodiments of the invention, especially for vaccine purposes, will contain additional nucleotide substitutions and/or deletions, designed to minimize the probability of reversion, and to minimize the probability of other flanking residues mutating to basic residues such as lysine and arginine and thereby restoring a functional NLS motif in the region.

The subject invention further provides a method for protecting a porcine animal from infection by a PRRS virus, which comprises vaccinating the animal with an amount of the above-recited vaccine that is effective to produce immunoprotection against infection by a PRRS virus.

The invention provides a method for making a genetically modified PRRS virus, which method comprises mutating the DNA sequence encoding an infectious RNA molecule which encodes the PRRS virus as described above, and expressing the genetically modified PRRS virus using a suitable expression system.

A PRRS virus, either wild-type or genetically modified, can be expressed from an isolated polynucleotide molecule using suitable expression systems generally known in the art, examples of which are described in this application. For example, the isolated polynucleotide molecule can be in the form of a plasmid capable of expressing the encoded virus in a suitable host cell in vitro, as is described in further detail below.

Other features of the invention will be evident upon review.

DETAILED DESCRIPTION OF THE INVENTION

We disclose herein a method of attenuating a virulent PRRS virus by mutating or deleting the NLS-2 region, NoLS region, or the NES region in the nucleocapsid or N protein (encoded by ORF7) of the virus, an immunogenic composition comprising said attenuated virus, and a method of protecting swine from PRRS by vaccination with said immunogenic compositions. PRRS viruses that have been attenuated by this method should retain the antigenic characteristics of the virulent field strain and therefore afford more potent protection than vaccines based on cell culture attenuated viruses.

The nucleocapsid protein (N) of PRRSV, which is encoded by ORF7, is a small basic protein that is phosphorylated (Wootton, Rowland, and Yoo, 2002) and forms homodimers (Wootton and Yoo, 2003). The crystal structure has recently been determined (Doan and Dokland, 2003). The N protein appears to have multiple functions in the infected cell. In addition to forming a spherical capsid structure into which genomic RNA is packaged, a process that takes place in the cytoplasm, a portion of N protein is transported into the nucleus and specifically to the nucleolus of the infected cell. The amino acid sequence of N protein contains two nuclear localization signals (NLS), a nucleolar localization signal (NoLS), and a nuclear export signal (NES) that facilitate transport into the nucleus and nucleolus, and export from the nucleus, respectively (Rowland et al., 1999; Rowland et al., 2003; Rowland and Yoo, 2003). While in the nucleolus, the N protein interacts with the small nucleolar RNA-associated protein fibrillarin and may regulate rRNA processing and ribosome biogenesis in the infected cell in order to favor virus replication (Yoo et al., 2003). In the current invention, we show that mutations and deletions within the NLS, NoLS, and NES motifs of the N protein can result in viable viruses with aberrant nuclear trafficking, and that viruses containing such mutations are useful as vaccines against PRRS.

Viral mutations of this type are valuable, either alone or in combination with other attenuating mutations, for designing novel PRRS vaccines.

DEFINITIONS

"An effective immunoprotective response", "immunoprotection", and like terms, for purposes of the present invention, mean an immune response that is directed against one or more antigenic epitopes of a pathogen so as to protect against infection by the pathogen in a vaccinated animal. For purposes of the present invention, protection against infection by a pathogen includes not only the absolute prevention of infection, but also any detectable reduction in the degree or rate of infection by a pathogen, or any detectable reduction in the severity of the disease or any symptom or condition resulting from infection by the pathogen in the vaccinated animal as compared to an unvaccinated infected animal. An effective immunoprotective response can be induced in animals that have not previously been infected with the pathogen and/or are not infected with the pathogen at the time of vaccination. An effective immunoprotective response can also be induced in an animal already infected with the pathogen at the time of vaccination.

A genetically modified PRRS virus is "attenuated" if it is less virulent than its unmodified parental strain. A strain is "less virulent" if it shows a statistically significant decrease in one or more parameters determining disease severity. Such parameters may include level of viremia, fever, severity of respiratory distress, severity of reproductive symptoms, or number or severity of lung lesions, etc.

"European PRRS virus" refers to any strain of PRRS virus having the genetic characteristics associated with the PRRS virus that was first isolated in Europe around 1991 (see, e.g., Wensvoort, G., et al., 1991, Vet. Q. 13:121-130). "European PRRS virus" is also sometimes referred to in the art as "Lelystad virus".

"Genetically modified", as used herein and unless otherwise indicated, means genetically mutated by human intervention, "mutated" means the replacement of an amino acid for another or the replacement of the coding nucleotide by another (e.g. C for a T), i.e., a so-called "substitution", preferably in a way that the encoded amino acid is changed, or any other mutation such as "deletion" or "insertion". The mutation is always carried out in the coding nucleotide sequence.

"Host cell capable of supporting PRRS virus replication" means a cell line which is capable of generating infectious PRRS when infected with a virus of the invention. Such cells include porcine alveolar macrophage cells and derivatives of porcine alveolar macrophage cells, MA-104 cells and derivatives of MA-104 cells, MARC-145 cells and derivatives of MARC-145 cells, and cells transfected with a receptor for the PRRS virus. Especially preferred for the demonstrating the small plaque phenotype of the invention are MARC-145 cells. The term "host cell capable of supporting PRRS virus replication" may also include cells within a live pig.

"Immune response" for purposes of this invention means the production of antibodies and/or cells (such as T lymphocytes) that are directed against, or assist in the decomposition or inhibition of, a particular antigenic epitope or particular antigenic epitopes.

"North American PRRS virus" means any PRRS virus having genetic characteristics associated with a North American PRRS virus isolate, such as, but not limited to the PRRS virus that was first isolated in the United States around the early 1990's (see, e.g., Collins, J. E., et al., 1992, J. Vet. Diagn. Invest. 4:117-126); North American PRRS virus isolate MN-1b (Kwang, J. et al., 1994, J. Vet. Diagn. Invest. 6:293-296); the Quebec LAF-exp91 strain of PRRS (Mardassi, H. et al., 1995, Arch. Virol. 140:1405-1418); and North American PRRS virus isolate VR 2385 (Meng, X.-J et al., 1994, J. Gen. Virol. 75:1795-1801). Genetic characteristics refer to genomic nucleotide sequence similarity and amino acid sequence similarity shared by North American PRRS virus strains.

"Open reading frame", or "ORF", as used herein, means the minimal nucleotide sequence required to encode a particular PRRS virus protein without an intervening stop codon.

"Porcine" and "swine" are used interchangeably herein and refer to any animal that is a member of the family Suidae such as, for example, a pig. The term "PRRS virus", as used herein, unless otherwise indicated, means any strain of either the North American or European PRRS viruses.

"PRRS" encompasses disease symptoms in swine caused by a PRRS virus infection. Examples of such symptoms include, but are not limited to, fever, abortion in pregnant females, respiratory distress, lung lesions, loss of appetite, and mortality in young pigs. As used herein, a PRRS virus that is "unable to produce PRRS" refers to a virus that can infect a pig, but which does not produce any disease symptoms normally associated with a PRRS infection in the pig.

PRRSV "N protein" or "ORF7" as used herein is defined as a polypeptide that is encoded by ORF7 of both the European and North American genotypes of PRRS virus. Examples of specific isotypes of N protein which are currently known are the 123 amino acid polypeptide of the North American PRRS prototype isolate VR2322 reported in Genbank by Accession numbers PRU87392, and the 128 residue N protein of European prototype PRRS isolate Lelystad reported in Genbank Accession number A26843.

"PRRSV N protein NLS-1 region" or "PRRSV ORF7 NLS-1 region" refers to a "pat4" or "nuc1" nuclear localization signal (Nakai & Kanehisa, 1992; Rowland & Yoo, 2003) containing four continuous basic amino acids (lysine or arginine), or three basic residues and a histidine or proline, located within about the first 15 N-terminal residues of the mature N protein. By way of example the VR2332 NLS-1 region sequence is KRKK and is located at residues 9-12, while the Lelystad isolate sequence is KKKK and is located at residues 10-13 of the N protein.

"PRRSV N protein NLS-2 region" or "PRRSV ORF7 NLS-2 region" refers to a second nuclear localization signal within the N protein that can take one of two forms. In North American PRRS viruses NLS-2 has a pattern which we have designated as the "pat8" motif, which begins with a proline followed within three residues by a five residue sequence containing at least three basic residues (K or R) out of five (a slight modification of the "pat7" or "nuc2" motif described by Nakai & Kanehisa, 1992; Rowland & Yoo, 2003). By way of example such a sequence is located at N protein residues 41-47 of the North American PRRSV isolate VR2332, and is represented by the sequence PGKKNKKK (SEQ ID NO: 1). In European PRRS viruses NLS-2 has a "pat4" or "nuc1" motif, which is a continuous stretch of four basic amino acids or three basic residues associated with histidine or proline (Nakai & Kanehisa, 1992; Rowland & Yoo, 2003). The NLS-2 of the European PRRSV isolate Lelystad is located at residues 47-50 and is represented by the sequence KKKK.

"PRRSV N protein NoLS region" or "PRRSV ORF7 NoLS region" refers to a nucleolar localization signal having a total length of about 32 amino acids and incorporating the NLS-2 region near its amino terminus. By way of example the VR2332 NoLS region sequence is located at residues 41-72 and is represented by the sequence PGKKNKKKNPEKPH-FPLATEDDVRHHFTPSER (SEQ ID NO: 2) (Rowland & Yoo, 2003) and the corresponding Lelystad isolate sequence is located at residues 42-73 and is represented by the sequence PRGGQAKKKKPEKPHFPLAAEDDIRHHLTQTER (SEQ ID NO: 3).

"PRRSV N protein NES region" or "PRRSV ORF7 NES region" refers to a nuclear export signal containing an LXL motif located near the carboxy terminal end of the N protein. The NES motif is X-R(2-5)-X-R2-X-R-Y where X is either leucine, isoleucine, or valine, Y either leucine, isoleucine, valine or alanine and R is any amino acid. As shown below the prototype North American and European isolates conform to this scheme with both having a 5-residue spacer.

"Transfected host cell" means practically any host cell which as described in U.S. Pat. No. 5,600,662 when transfected with PRRS virus RNA can produce a first round of PRRS virions. If further productive infection is desired a "host cell capable of supporting PRRS virus replication" as defined below would be used.

Polynucleotide molecules can be genetically mutated using recombinant techniques known to those of ordinary skill in the art, including by site-directed mutagenesis, or by random mutagenesis such as by exposure to chemical mutagens or to radiation, as known in the art." Said mutations may be carried out by standard methods known in the art, e.g. site directed mutagenesis (see e.g. Sambrook et al.(1989) Molecular Cloning: A Laboratory Manual, 2 (nd)ed., Cold Spring Harbor Laboratory Press, Cold Spring Harbor, N.Y.) of an infectious copy as described (e.g. Meulenberg et al., Adv. Exp. Med. Biol, 1998, 440:199-206).

Accordingly, the subject invention further provides a method for making a genetically modified North American PRRS virus, which method comprises mutating the DNA sequence encoding an infectious RNA molecule which encodes the PRRS virus as described above, and expressing the genetically modified PRRS virus using a suitable expression system. A genetically modified PRRS virus can be expressed from an isolated polynucleotide molecule using suitable expression systems generally known in the art, examples of which are described in this application. For example, the isolated polynucleotide molecule can be in the form of a plasmid capable of expressing the encoded virus in a suitable host cell in vitro, as is described in further detail below.

The North American PRRSV N protein sequences are highly conserved and the reported sequences have about 93-100% identity with each other. The North American and European PRRSV N proteins are about 57-59% identical and share common structural motifs.

By way of example the VR2332 NES region sequence is located at residues 106-117 and is represented by the sequence LPTHHTVRLIRV (SEQ ID NO: 4) (Rowland & Yoo, 2003) and the Lelystad isolate sequence is located at residues 107-118 and is represented by the sequence LPVAHTVRLIRV (SEQ ID NO: 5).

In the consensus below, which includes all sequences in North American PRRSV sequences in Genbank, the positions with a (*) are completely conserved. Alternative amino acids are shown under each position.

```
LPTHHTVRLIRV(SEQ ID NO: 4)
VAQ****A
    Q
    V
    G
```

The numbering of amino acids referenced above is according to the database entries mentioned. In all other PRRS isolates, which might be numbered differently, identification of the proper regions are readily achieved by identifying preserved characteristic amino acids in a PRRS strain of interest and aligning it with a reference strain. It is an object of the present invention to modify a PRRS virus or its encoding nucleic acids such that one or more conserved regions are eliminated either by substitution, deletion, or insertion such that it results in an attenuated phenotype.

Deletions, insertions, or substitutions which eliminate the conserved NLS-2 motif, the NoLS region, or the NES motif are introduced by modification of polynucleotides in the encoding viruses of the invention. In a preferred embodiment, a deletion or insertion comprising 1, 2, 3, 4 or 5 amino acids results in the elimination of a conserved motif and results in an attenuated virus Amino acids can be classified according to physical properties and contribution to secondary and tertiary protein structure. A conservative substitution is recognized in the art as a substitution of one amino acid for another amino acid that has similar properties. Exemplary conservative substitutions are set out in Table 1 (from WO 97/09433, page 10, published Mar. 13, 1997 (PCT/GB96/02197, filed Sep. 6, 1996)), immediately below.Table 1 Conservative Substitutions I

| SIDE CHAIN CHARACTERISTIC | AMINO ACID |
| --- | --- |
| Aliphatic | |
| Non-polar | G A P |
| | I L V |
| Polar-uncharged | C S T M |
| | N Q |
| Polar-charged | D E |
| | K R |
| Aromatic | H F W Y |
| Other | N Q D E |

Alternatively, conservative amino acids can be grouped as described in Lehninger, [Biochemistry, Second Edition; Worth Publishers, Inc. NY:NY (1975), pp. 71-77] as set out in Table 2, immediately below

TABLE 2

Conservative Substitutions II

| SIDE CHAIN CHARACTERISTIC | AMINO ACID |
| --- | --- |
| Non-polar (hydrophobic) | |
| A. Aliphatic: | A L I V P |
| B. Aromatic: | F W |
| C. Sulfur-containing: | M |
| D. Borderline: | G |
| Uncharged-polar | |
| A. Hydroxyl: | S T Y |
| B. Amides: | N Q |
| C. Sulfhydryl: | C |
| D. Borderline: | G |

TABLE 2-continued

Conservative Substitutions II

| SIDE CHAIN CHARACTERISTIC | AMINO ACID |
|---|---|
| Positively Charged (Basic): | K R H |
| Negatively Charged (Acidic): | D E |

As still an another alternative, exemplary conservative substitutions are set out in Table 3, immediately below.

TABLE 3

Conservative Substitutions III

| Original Residue | Exemplary Substitution |
|---|---|
| Ala (A) | Val, Leu, Ile |
| Arg (R) | Lys, Gln, Asn |
| Asn (N) | Gln, His, Lys, Arg |
| Asp (D) | Glu |
| Cys (C) | Ser |
| Gln (Q) | Asn |
| Glu (E) | Asp |
| His (H) | Asn, Gln, Lys, Arg |
| Ile (I) | Leu, Val, Met, Ala, Phe, |
| Leu (L) | Ile, Val, Met, Ala, Phe |
| Lys (K) | Arg, Gln, Asn |
| Met (M) | Leu, Phe, Ile |
| Phe (F) | Leu, Val, Ile, Ala |
| Pro (P) | Gly |
| Ser (S) | Thr |
| Thr (T) | Ser |
| Trp (W) | Tyr |
| Tyr (Y) | Trp, Phe, Thr, Ser |
| Val (V) | Ile, Leu, Met, Phe, Ala |

Preparation of Genetically Modified PRRS Virus

Recombinant DNA technology comprises extremely varied and powerful molecular biology techniques aimed at modifying nucleic acids at the DNA level and makes it possible to analyze and modify genomes at the molecular level. In this respect, viruses such as the PRRS virus because of the small size of its genome is particularly amenable to such manipulations. However, recombinant DNA technology is not immediately applicable to nonretroviral RNA viruses because these viruses do not encompass a DNA intermediate step in their replication. For such viruses infectious cDNA clones have to be developed before recombinant DNA technology can be applied to their genome to generate modified virus. Infectious clones can be derived through the construction of full-length (genomic length) cDNA (here used in the broad sense of a DNA copy of RNA and not only in the strict sense of a DNA copy of mRNA) of the virus under study after which an infectious transcript is synthesized in vivo in cells transfected with the full-length cDNA, but infectious transcripts can also be obtained by in vitro transcription from in vitro ligated partial-length cDNA fragments that comprise the full viral genome. In all cases, the transcribed RNA carries all the modifications that have been introduced to the cDNA and can be used to further passage the thus modified virus.

The preparation of an infectious clone of a European PRRS virus isolate or Lelystad virus is described in U.S. Pat. No. 6,268,199 which is hereby fully incorporated by reference. The preparation of an infectious cDNA clone of a North American PRRS virus isolate designated P129 (Lee et al., 2005; Yoo et al., 2004) is described in U.S. Pat. No. 6,500,662 which is hereby incorporated fully by reference. The sequence of P129 cDNA is disclosed in Genbank Accession Number AF494042 and in U.S. Pat. No. 6,500,662. Our work below makes use of such an infectious clone which in the context of a plasmid is expressed by the CMV immediate early promoter and has been designated pCMV-S—P129 and is also disclosed within U.S. Pat. No. 6,500,662. As described in U.S. Pat. No. 6,500,662 there are other plasmids and promoters suitable for use here.

Given the complete sequence of any open reading frame of interest and the location of an amino acid residue of interest, one of ordinary skill need merely consult a codon table to design changes at the particular position desired.

A table of amino acids and their representative abbreviations, symbols and codons is set forth below in the following Table 4.

TABLE 4

| Amino acid | Abbrev. | Symbol | Codon(s) | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

Codons constitute triplet sequences of nucleotides in mRNA and their corresponding cDNA molecules. Codons are characterized by the base uracil (U) when present in a mRNA molecule but are characterized by base thymidine (T) when present in DNA. A simple change in a codon for the same amino acid residue within a polynucleotide will not change the sequence or structure of the encoded polypeptide. It is apparent that when a phrase stating that a particular 3 nucleotide sequence "encode(s)" any particular amino acid, the ordinarily skilled artisan would recognize that the table above provides a means of identifying the particular nucleotides at issue. By way of example, if a particular three nucleotide sequence encodes lysine, the table above discloses that the two possible triplet sequences are AAA and AAG. Glycine is encoded by GGA, GGC, GGT (GGU if in RNA) and GGG. To change a lysine to glycine residue in an encoded protein one might replace a AAA or AAG triplet with any of by GGA and GGC, GGT or GGG in the encoding nucleic acid. The coding sequence of the N or ORF7 protein from the P129 isolate is exemplified below.

TABLE 5

Coding Sequence from N protein of P129 isolate

```
 M   P   N   N   N   G   K   Q   Q   K   K   K¹²
ATG CCA AAT AAC AAC GGC AAG CAG CAA AAG AAA AAG³⁶

K   G   N   G   Q   P   V   N   Q   L   C   Q²⁴
AAG GGG AAT GGC CAG CCA GTC AAT CAG CTG TGC CAG⁷²

M   L   G   K   I   I   A   Q   Q   N   Q   S³⁶
ATG CTG GGT AAA ATC ATC GCC CAG CAA AAC CAG TCC¹⁰⁸

R   G   K   G   P   G   K   K   S   K   K   K⁴⁸
AGA GGC AAG GGA CCG GGC AAG AAA AGT AAG AAG AAA¹¹⁴

N   P   E   K   P   H   F   P   L   A   T   E⁶⁰
AAC CCG GAG AAG CCC CAT TTT CCT CTA GCG ACC GAA²⁸⁸

D   D   V   R   H   H   F   T   P   G   E   R⁷²
GAT GAC GTC AGG CAT CAC TTC ACC CCT GGT GAG CGG³²⁴

Q   L   C   L   S   S   I   Q   T   A   F   N⁸⁴
CAA TTG TGT CTG TCG TCG ATC CAG ACT GCC TTT AAC²⁵²

Q   G   A   G   T   C   T   L   S   D   S   G⁹⁶
CAG GGC GCT GGA ACT TGT ACC CGT TCA GAT TCA GGG²⁸⁸

R   I   S   Y   T   V   E   F   S   L   P   T¹⁰⁸
AGG ATA AGT TAC ACT GTG GAG TTT AGT TTG CCG ACG³²⁴

H   H   T   V   R   L   I   R   V   T   A   S¹²⁰
CAT CAT ACT GTG CGC CTG ATC CGC GTC ACA GCA TCA³⁶⁰

P   S   A¹²³      (SEQ ID NO: 6)
CCC TCA GCA³⁶⁹    (SEQ ID NO: 7)
```

The construction of a mutant protein N polynucleotide sequence modified in the NLS-2 regions is demonstrated by way of illustrative example in Example 2.

It will be appreciated that mutations in the NLS-1, NoLS or NES regions can be accomplished with similar techniques and similar results.

Demonstration that a Genetically Modified PRRS Virus is Attenuated

To demonstrate that a particular genetically modified strain is attenuated an experiment as described below might be used.

At least 10 gilts per group are included in each trial, which are derived from a PRRSV-free farm. Animals are tested free of PRRS virus specific serum antibodies and negative for PRRSV. All animals included in the trial are of the same source and breed. The allocation of the animals to the groups is randomized.

Challenge is performed at day 90 of pregnancy with intra-nasal application of 1 ml PRRSV with $10^5 TCID_{50}$ per nostril. There are at least three groups for each test setup: One group for P129 challenge; one test group for challenge with the possibly attenuated virus; and one strict control group.

The study is deemed valid when the strict controls stay PRRSV-negative over the time course of the study and at least 25% less live healthy piglets are born in the P129 challenged group compared to the strict controls.

Attenuation, in other words less virulence, is defined as the statistical significant change of one or more parameters determining reproductive performance or other symptomology:

Significant reduction in at least one of the following parameters for the test group (possibly attenuated virus) compared to the unmodified parental strain infected group would be an indication of attenuation:
a) frequency of stillborns
b) abortion at or before day 112 of pregnancy
c) number of mummified piglets
d) number of less lively and weak piglets
e) preweaning mortality Furthermore a significant increase in one of the following parameters for the test group compared the unmodified parental strain infected group is preferred:

f) number of piglets weaned per sow
g) number of live healthy piglets born per sow In the alternative, respiratory symptoms and other symptoms of PRRSV infection could be examined to establish attenuation as described in Example 3 below Vaccines An attenuated strain is valuable for the formulation of vaccines. The present vaccine is effective if it protects a pig against infection by a PRRS virus. A vaccine protects a pig against infection by a PRRS virus if, after administration of the vaccine to one or more unaffected pigs, a subsequent challenge with a biologically pure virus isolate (e.g., VR 2385, VR 2386, P129 etc.) results in a lessened severity of any gross or histopathological changes (e.g., lesions in the lung) and/or of symptoms of the disease, as compared to those changes or symptoms typically caused by the isolate in similar pigs which are unprotected (i.e., relative to an appropriate control). More particularly, the present vaccine may be shown to be effective by administering the vaccine to one or more suitable pigs in need thereof, then after an appropriate length of time (e.g., 3 weeks), challenging with a large sample (10$^{(3-7)}$TCID$_{(50)}$) of a biologically pure PRRSV isolate. A blood sample is then drawn from the challenged pig after about one week, and an attempt to isolate the virus from the blood sample is then performed (e.g., see the virus isolation procedure exemplified in Experiment VIII below). Isolation of a large amount of the virus is an indication that the vaccine may not be effective, while isolation of reduced amounts of the virus (or no virus) is an indication that the vaccine may be effective.

Thus, the effectiveness of the present vaccine may be evaluated quantitatively (i.e., a decrease in the percentage of consolidated lung tissue as compared to an appropriate control group) or qualitatively (e.g., isolation of PRRSV from blood, detection of PRRSV antigen in a lung, tonsil or lymph node tissue sample by an immunoassay). The symptoms of the porcine reproductive and respiratory disease may be evaluated quantitatively (e.g., temperature/fever), semi-quantitatively (e.g., severity of respiratory distress [explained in detail below], or qualitatively (e.g., the presence or absence of one or more symptoms or a reduction in severity of one or more symptoms, such as cyanosis, pneumonia, lung lesions etc.).

An unaffected pig is a pig which has either not been exposed to a porcine reproductive and respiratory disease infectious agent, or which has been exposed to a porcine reproductive and respiratory disease infectious agent but is not showing symptoms of the disease. An affected pig is one which shows symptoms of PRRS or from which PRRSV can be isolated.

Vaccines of the present invention can be formulated following accepted convention to include acceptable carriers for animals, including humans (if applicable), such as standard buffers, stabilizers, diluents, preservatives, and/or solubilizers, and can also be formulated to facilitate sustained release. Diluents include water, saline, dextrose, ethanol, glycerol, and the like. Additives for isotonicity include sodium chloride, dextrose, mannitol, sorbitol, and lactose, among others. Stabilizers include albumin, among others. Other suitable vaccine vehicles and additives, including those that are particularly useful in formulating modified live vaccines, are known or will be apparent to those skilled in the art. See, e.g., Remington's Pharmaceutical Science, 18th ed., 1990, Mack Publishing, which is incorporated herein by reference.

Vaccines of the present invention can further comprise one or more additional immunomodulatory components such as, e.g., an adjuvant or cytokine, among others. Non-limiting examples of adjuvants that can be used in the vaccine of the present invention include the RIBI adjuvant system (Ribi Inc., Hamilton, Mont.), alum, mineral gels such as aluminum hydroxide gel, oil-in-water emulsions, water-in-oil emulsions such as, e.g., Freund's complete and incomplete adjuvants, Block copolymer (CytRx, Atlanta, Ga.), QS-21 (Cambridge Biotech Inc., Cambridge Mass.), SAF-M (Chiron, Emeryville Calif.), AMPHIGEN® adjuvant, saponin, Quil A or other saponin fraction, monophosphoryl lipid A, and Avridine lipid-amine adjuvant. Non-limiting examples of oil-in-water emulsions useful in the vaccine of the invention include modified SEAM62 and SEAM 1/2 formulations. Modified SEAM62 is an oil-in-water emulsion containing 5% (v/v) squalene (Sigma), 1% (v/v) SPAN® 85 detergent (ICI Surfactants), 0.7% (v/v) TWEEN® 80 detergent (ICI Surfactants), 2.5% (v/v) ethanol, 200 pg/ml Quil A, 100 [mgr]g/ml cholesterol, and 0.5% (v/v) lecithin. Modified SEAM 1/2 is an oil-in-water emulsion comprising 5% (v/v) squalene, 1% (v/v) SPAN® 85 detergent, 0.7% (v/v) Tween 80 detergent, 2.5% (v/v) ethanol, 100 µg/ml Quil A, and 50 µg/ml cholesterol. Other immunomodulatory agents that can be included in the vaccine include, e.g., one or more interleukins, interferons, or other known cytokines.

Vaccines of the present invention can optionally be formulated for sustained release of the virus, infectious RNA molecule, plasmid, or viral vector of the present invention. Examples of such sustained release formulations include virus, infectious RNA molecule, plasmid, or viral vector in combination with composites of biocompatible polymers, such as, e.g., poly(lactic acid), poly(lactic-co-glycolic acid), methylcellulose, hyaluronic acid, collagen and the like. The structure, selection and use of degradable polymers in drug delivery vehicles have been reviewed in several publications, including A. Domb et al., 1992, Polymers for Advanced Technologies 3: 279-292, which is incorporated herein by reference. Additional guidance in selecting and using polymers in pharmaceutical formulations can be found in texts known in the art, for example M. Chasin and R. Langer (eds), 1990, "Biodegradable Polymers as Drug Delivery Systems" in: Drugs and the Pharmaceutical Sciences, Vol. 45, M. Dekker, N.Y., which is also incorporated herein by reference. Alternatively, or additionally, the virus, plasmid, or viral vector can be microencapsulated to improve administration and efficacy. Methods for microencapsulating antigens are well-known in the art, and include techniques described, e.g., in U.S. Pat. No. 3,137,631; U.S. Pat. No. 3,959,457; U.S. Pat. No. 4,205,060; U.S. Pat. No. 4,606,940; U.S. Pat. No. 4,744,933; U.S. Pat. No. 5,132,117; and International Patent Publication WO 95/28227, all of which are incorporated herein by reference.

Liposomes can also be used to provide for the sustained release of virus, plasmid, or viral vector. Details concerning how to make and use liposomal formulations can be found in, among other places, U.S. Pat. No. 4,016,100; U.S. Pat. No. 4,452,747; U.S. Pat. No. 4,921,706; U.S. Pat. No. 4,927,637; U.S. Pat. No. 4,944,948; U.S. Pat. No. 5,008,050; and U.S. Pat. No. 5,009,956, all of which are incorporated herein by reference.

An effective amount of any of the above-described vaccines can be determined by conventional means, starting with a low dose of virus, plasmid or viral vector, and then increasing the dosage while monitoring the effects. An effective amount may be obtained after a single administration of a vaccine or after multiple administrations of a vaccine. Known factors can be taken into consideration when determining an optimal dose per animal. These include the species, size, age and general condition of the animal, the presence of other drugs in the animal, and the like. The actual dosage is preferably chosen after consideration of the results from other animal studies.

One method of detecting whether an adequate immune response has been achieved is to determine seroconversion and antibody titer in the animal after vaccination. The timing of vaccination and the number of boosters, if any, will preferably be determined by a doctor or veterinarian based on analysis of all relevant factors, some of which are described above.

The effective dose amount of virus, infectious RNA molecule, plasmid, or viral vector, of the present invention can be determined using known techniques, taking into account factors that can be determined by one of ordinary skill in the art such as the weight of the animal to be vaccinated. The dose amount of virus of the present invention in a vaccine of the present invention preferably ranges from about $10^1$ to about $10^9$ pfu (plaque forming units), more preferably from about $10^2$ to about $10^8$ pfu, and most preferably from about $10^3$ to about $10^7$ pfu. The dose amount of a plasmid of the present invention in a vaccine of the present invention preferably ranges from about 0.1 µg to about 100 mg, more preferably from about 1 µg to about 10 mg, even more preferably from about 10 µg to about 1 mg. The dose amount of an infectious RNA molecule of the present invention in a vaccine of the present invention preferably ranges from about 0.1 to about 100 mg, more preferably from about 1 µg to about 10 mg, even more preferably from about 10 µg to about 1 mg. The dose amount of a viral vector of the present invention in a vaccine of the present invention preferably ranges from about $10^1$ pfu to about $10^9$ pfu, more preferably from about $10^2$ pfu to about $10^8$ pfu, and even more preferably from about $10^3$ to about $10^7$ pfu. A suitable dosage size ranges from about 0.5 ml to about 10 ml, and more preferably from about 1 ml to about 5 ml.

By way of example, vaccines may be delivered orally, parenterally, intradermally, subcutaneously, intramuscularly, intranasally or intravenously. Oral delivery may encompass, for example, adding the compositions to the feed or drink of the animals. Factors bearing on the vaccine dosage include, for example, the weight and age of the pig.

The present invention further provides a method of preparing a vaccine comprising a PRRS virus, infectious RNA molecule, plasmid, or viral vector described herein, which method comprises combining an effective amount of one of the PRRS virus, infectious RNA molecule, plasmid, or viral vector of the present invention, with a carrier acceptable for pharmaceutical or veterinary use.

In addition the live attenuated vaccine of the present invention can be modified as described in U.S. Pat. No. 6,500,662 to encode a heterologous antigenic epitope which is inserted into the PRRS viral genome using known recombinant techniques. Antigenic epitopes useful as heterologous antigenic epitopes for the present invention include antigenic epitopes from a swine pathogen other than PRRS virus which include, but are not limited to, an antigenic epitope from a swine pathogen selected from the group consisting of porcine parvovirus, porcine circovirus, a porcine rotavirus, swine influenza, pseudorabies virus, transmissible gastroenteritis virus, porcine respiratory coronavirus, classical swine fever virus, African swine fever virus, encephalomyocarditis virus, porcine paramyxovirus, *Actinobacillus pleuropneumoniae, Actinobacillus suis, Bacillus anthraci, Bordetella bronchiseptica, Clostridium haemolyticum, Clostridium perfringens,*

Clostridium tetani, Escherichia coli, Erysipelothdix rhusiopathiae, Haemophilus parasuis, Leptospira spp., Mycoplasma hyopneumoniae, Mycoplasma hyorhinis, Mycoplasma hyosynovia, Pasteurella multocida, Salmonella choleraesuis, Salmonella typhimurium, Streptococcus equismilis, and Streptococcus suis. Nucleotide sequences encoding antigenic epitopes from the aforementioned swine pathogens are known in the art and can be obtained from public gene databases such as GenBank (http://www.ncbi.nlm.nih.gov/Web/Genbank/index.html) provided by NCBI.

Additional features and variations of the invention will be apparent to those skilled in the art from the entirety of this application, including the detailed description, and all such features are intended as aspects of the invention. Likewise, features of the invention described herein can be re-combined into additional embodiments that also are intended as aspects of the invention, irrespective of whether the combination of features is specifically mentioned above as an aspect or embodiment of the invention. Also, only such limitations which are described herein as critical to the invention should be viewed as such; variations of the invention lacking limitations which have not been described herein as critical are intended as aspects of the invention. It will be clear that the invention may be practiced otherwise than as particularly described in the foregoing description and examples.

Numerous modifications and variations of the present invention are possible in light of the above teachings and, therefore, are within the scope of the invention.

The present invention is further illustrated by, but not limited to, the following examples

EXAMPLE 1

Construction of Shuttle Plasmid
pTB-Shuttle-PRRSV-3997

A shuttle plasmid was constructed in order to facilitate the introduction of specific modifications to a full-length PRRS virus genomic cDNA clone. A 3,997 bp fragment, representing the extreme 3' end of the viral genome (nucleotide positions 11,504 to 15,416, including a 21 residue polyadenosine tail) and 84 bp of downstream vector sequences, was PCR-amplified. The PCR reaction included 5 ng of pCMV-S-P129 plasmid DNA (U.S. Pat. No. 6,500,662 B1), 300 ng of forward primer P-shuttle-Fwd (5'-ACTCAGTCTAAGTGCTGGAAAGTTATG-3') (SEQ ID NO: 8): positions 11,504 to 11,530), 300 ng of reverse primer P-shuttle-Rev primers (5'-ATCTTATCATGTCTGGATCCCCGCGGC-3') (SEQ ID NO: 9): positions 15,500 to 15,475), 1 mM each of dCTP, dGTP, dATP, and dTTP, 1×PCR buffer [10 mM KCl, 10 mM $(NH_4)_2SO_4$, 20 mM Tris-HCl (pH 8.8), 2 mM $MgSO_4$, 0.1% Triton X-100], and 2.5 U of Pfu DNA polymerase (Stratagene) using the GeneAmp PCR system 2400 (Perkin Elmer). The reaction was heated up for 5 min at 95° C. and subjected to 35 cycles of amplification under the following conditions; denaturation at 95° C. for 30 sec, primer annealing at 55° C. for 1 min, and extension at 72° C. for 3 min. The PCR product was cloned into the pTrueBlue vector using the TrueBlue MicroCartridge™ PCR Cloning Kit XL (Genomics One; Buffalo, N.Y.) to create pTB-shuttle-PRRSV-3997.

EXAMPLE 2

Modification of the NLS-2 Sequence to Generate
P129-GG Virus

PCR-based site-directed mutagenesis was used to modify the nuclear localization signal 2(NLS-2) motif located at amino acid positions 41 to 47 of the nucleocapsid (N) protein. Among North American genotype PRRS viruses, this NLS motif is generally PGKKNKK (as in the prototype isolate VR-2332 or the Canadian isolate PA-8), or a derivative thereof, such as PGKKSKK (found in isolates P129 and 93-47324). The presence of multiple positively charged lysine (K) or arginine (R) residues is believed to be important for a fully functional NLS signal. The lysine residues at positions 43 and 44 of N (nucleotide positions 14,999-15,004 of the P129 genome) were replaced by glycine residues using the shuttle plasmid and the mutagenic primer pair KK43/44GG-Fwd (5'-GGCAAGGGACCGGGA GGGGGAAATAAGAAGAAAAAC-3') (SEQ ID NO: 10)—: genome positions 14,984 to 15,019) and KK43/44GG-Rev (5'-GTTTTTCTTCTT ATTTCCCCCTCCCGGTCCCTTGCC-3') (SEQ ID NO: 11)—: genome positions 14,984 to 15,019), where underlines indicate codon changes for amino acid substitutions from KKS to GGN. PCR amplifications were carried out using 5 ng of pTB-shuttle-PRRSV-3997 plasmid DNA, 300 ng each of the forward and reverse primers; 1 mM concentrations each of dCTP, dGTP, dATP, and dTTP, 1×PCR buffer [10 mM KCl, 10 mM $(NH_4)_2SO_4$, 20 mM Tris-HCl (pH 8.8), 2 mM $MgSO_4$, 0.1% Triton X-100]; and 2.5 U of Pfu DNA polymerase (Stratagene). The samples were subjected to 16 cycles of amplification under the following conditions: denaturation at 94° C. for 30 s, primer annealing at 55° C. for 1 min, and primer extension at 68° C. for 12 min 30 sec. Following PCR cycling, the PCR-product was digested with 10 U of DpnI to remove the methylated plasmid DNA template. *E. coli* XL1-Blue cells were transformed by heat shock with 4 µl of the PCR-Dpn I digested reaction containing the mutated plasmids and plated on an LB agar plate containing ampicillin. Colonies were randomly picked and cultivated overnight. Plasmid DNA was prepared using a QIAprep spin miniprep kit (Qiagen). The presence of the desired mutation (PGGGNKK) was verified by nucleotide sequencing and the resulting plasmid was named pTB-shuttle-N-GG.

The shuttle plasmid carrying the GG mutation (pTB-shuttle-N-GG) and the wild type full-length genomic clone (pCMV-S—P129) each contain unique BsrG I and Spe I sites (at positions 1,192 and 3,963, and positions 12,692 and 15,463, respectively). After digestion with these two enzymes, the 2,772 bp BsrG I-Spe I fragment was gel-purified from pTB-shuttle-N-GG, and the 16,120 bp BsrG I-Spe I fragment was gel-purified from pCMV-S—P129. These two fragments were ligated using T4 DNA ligase (Invitrogen) to construct a GGN-modified full-length genomic cDNA clone. *E. coli* strain DH5-α was transformed with 10 µl of the ligation reaction. Bacterial colonies were selected from LB plates containing ampicillin and plasmid DNAs were prepared. Based on Xma I digestion patterns, full-length clones were selected. The selected clones were sequenced to confirm the presence of the GGN modification in the full-length genomic cDNA clone. One of the resulting plasmids was designated pCMV-S—P129-GG.

MARC-145 cells were grown in Dulbecco's modified Eagle medium (DMEM) supplemented with 8% fetal bovine serum (FBS; Gibco BRL), penicillin (100 U/ml), and streptomycin (50 µg/ml) at 37° C. with 5% $CO_2$ Cells were seeded in 35 mm-diameter dishes and grown to 70% confluency. The cells were transfected for 24 h with 2 µg of pCMV-S—P129-GG plasmid DNA using Lipofectin (Invitrogen). The transfected cells were incubated at 37° C. in DMEM supplemented with 8% FBS for 5 days. PRRSV-specific cytopathic effect (CPE) was observed from 3 days post-transfection and further spread to neighboring cells was seen by 5 days post-transfection. The specificity of CPE was confirmed by immunofluorescence cell staining using a rabbit antiserum for nonstructural proteins nsp2 and nsp3, and the N-specific MAb SDOW17 (see FIG. 1). The culture supernatants from transfected cells were harvested at 5 days post-transfection and designated 'P129-GG passage 1' (P1). The passage-I virus was used to inoculate fresh Marc-145 cells and the 5-day harvest was designated 'passage-2' (P2). 'Passage-3' (P3) virus was prepared in the same way as P2. Each viral passage was stored in 1 ml aliquots at −80° C. until use. Each passage of P129-GG virus was titrated by plaque assay, and the titers were determined to be $1\times10^2$, $5\times10^2$, and $5\times10^3$ pfu/ml for passages 1, 2, and 3, respectively. Wild type P129 virus was generated from pCMV-S—P129 and titrated in parallel, yielding titers of $1\times10^3$, $1\times10^4$, and $5\times10^5$ pfu/ml for passages 1, 2, and 3 respectively.

EXAMPLE 3

Infection of Pigs with P129-GG Virus and Parental P129 Virus (Demonstration that the P129-GG Virus is Attenuated)

Twenty-one healthy, crossbred pigs without a history of disease caused by or vaccination against PRRSV and *Mycoplasma hyopneumoniae* were randomly assigned to 3 treatment groups of 7 pigs each. At approximately 6 weeks of age, T01 pigs received a placebo while T02 and T03 pigs received an intranasal challenge with 2.0 ml of virus stock diluted to $2.5\times10^4$ pfu/ml ($5.0\times10^4$ pfu/dose) of the genetically modified P129-GG virus (generated from plasmid pCMV-S—P129-GG) or parental P129 PRRS virus (generated from plasmid pCMV-S—P129), respectively. All pigs were observed daily for clinical signs including general condition, depression, loss of appetite, sneezing, coughing, and respiratory distress. Rectal temperatures and body weights were recorded. Blood samples were taken on Days 0, 4, 7, 10, 14, 21, and 28 for PRRSV isolation and serology. Necropsies were performed on Days 14 (2 pigs/group) and 28 (5 pigs/group), and tissue samples (lung and tonsil) were collected. Estimates of lung lesion severity and percent consolidation of each lung lobe were made. Pigs in groups T02 and T03 developed signs of a mild PRRS virus infection, shed virus in the serum, and seroconverted. Uninfected control pigs (T01) remained negative for serum viremia and negative for antibody to the PRRS virus.

Figure 2C:
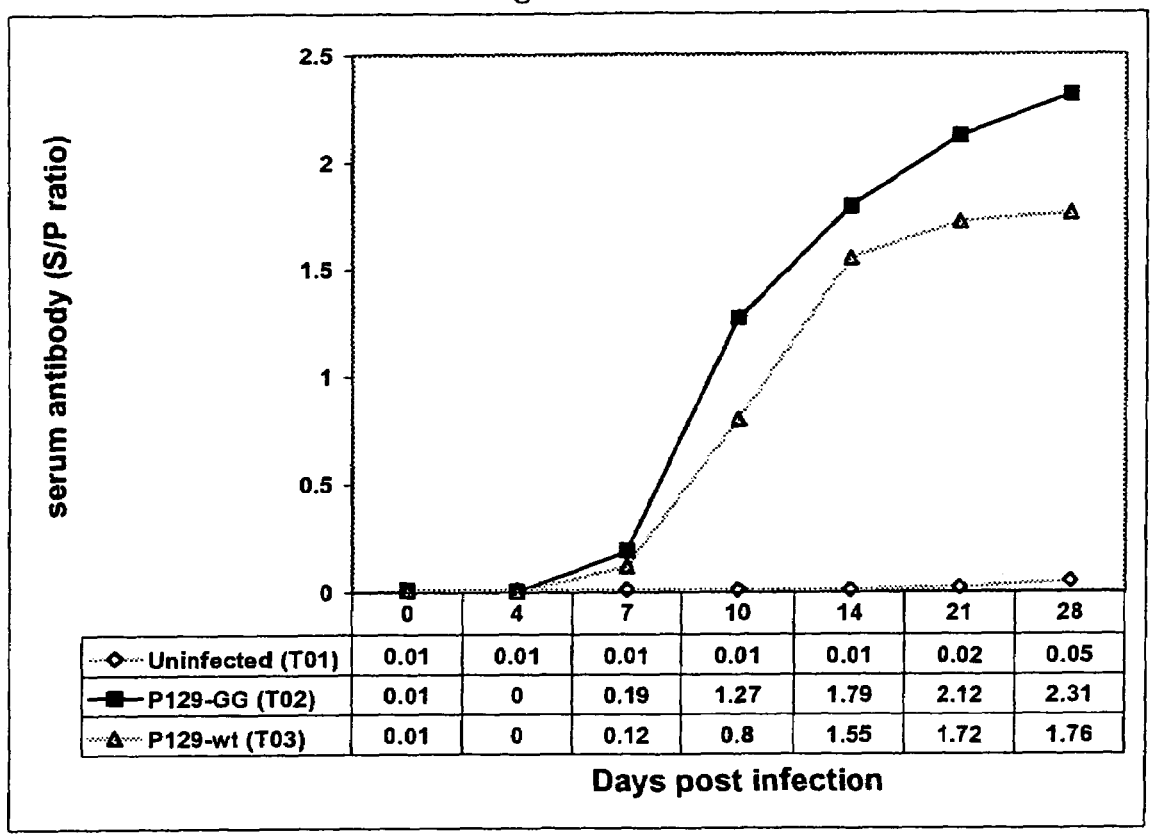
FIG. 2. (A) Number of pigs viremic on days 0 through 28 post infection by treatment groups (7 pigs per group). (B) Mean viral titer in the sera of pigs at days 0 through 28 post infection, by treatment group. (C) Mean ELISA antibody levels (S/P ratios) in the sera of pigs at days 0 through 28 post infection, by treatment group (D) a re-titration of the sera shown in FIG. 2C all samples were diluted 1:5 prior to assay in order to better distinguish differences in samples with high titers. (E) Mean serum neutralization titers in infected pigs during the four-week study
Figure 2D:
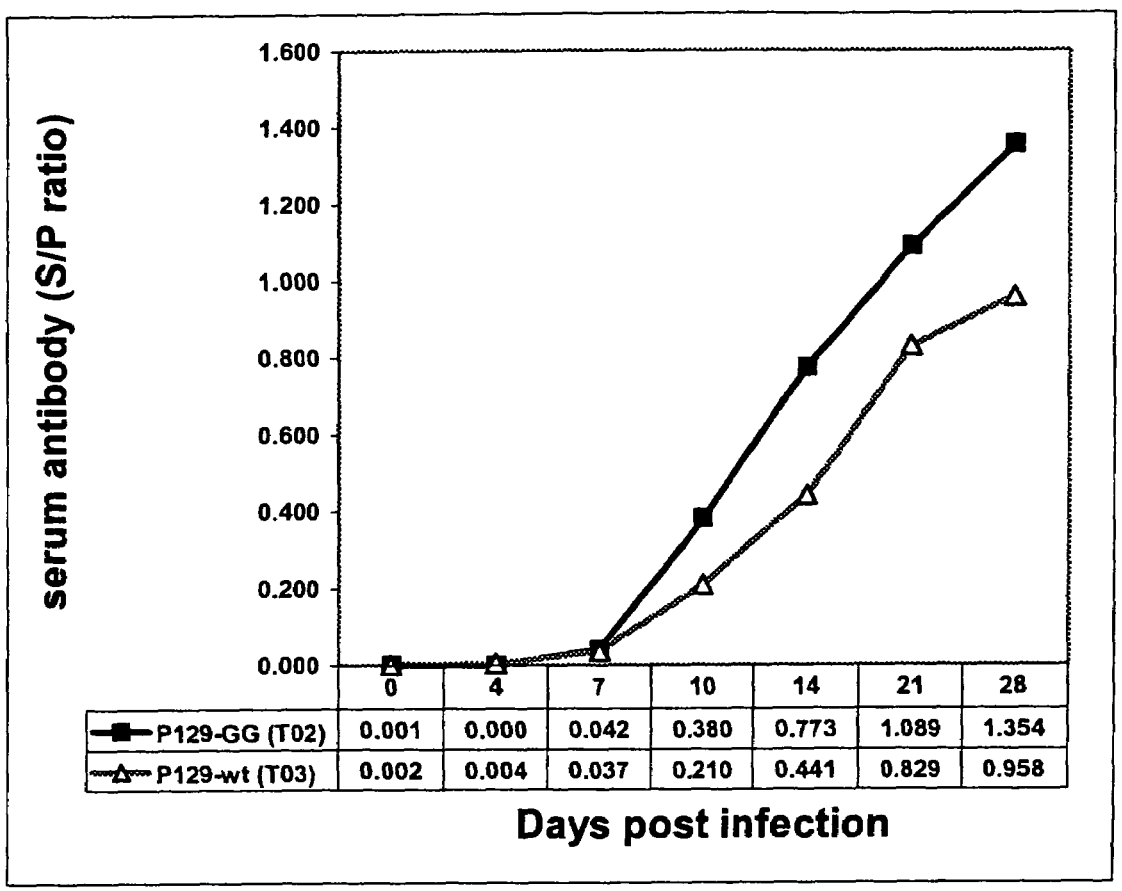

Compared to pigs infected with P129 parental virus (T03), pigs infected with the P129-GG virus (T02) shed less virus in their serum (FIGS. 2a and 2b) and produced higher levels of anti-PRRS ELISA antibody (FIGS. 2C and 2D), and neutralizing antibody (FIG. 2e).

TABLE 6

| ELISA Antibody Levels (S/P) | | | | | | | |
|---|---|---|---|---|---|---|---|
| | day 0 | day 4 | day 7 | day 10 | day 14 | day 21 | day 28 |
| P129-wt | | | | | | | |
| pig 28 | 0.000 | 0.000 | 0.061 | 0.283 | 0.527 | 0.689 | 1.025 |
| pig 30 | 0.006 | 0.000 | 0.044 | 0.178 | 0.527 | 0.731 | 0.672 |
| pig 35 | 0.000 | 0.000 | 0.000 | 0.027 | 0.157 | 0.241 | 0.197 |
| pig 40 | 0.004 | 0.021 | 0.030 | 0.208 | 0.575 | 0.723 | 0.890 |
| pig 43 | 0.000 | 0.000 | 0.049 | 0.354 | 0.419 | 1.760 | 2.006 |
| mean | 0.002 | 0.004 | 0.037 | 0.210 | 0.441 | 0.829 | 0.958 |
| P129-GG | | | | | | | |
| pig 33 | 0.000 | 0.000 | 0.000 | 0.356 | 0.873 | 1.377 | 1.705 |
| pig 36 | 0.000 | 0.000 | 0.019 | 0.383 | 1.038 | 1.536 | 1.604 |
| pig 38 | 0.000 | 0.000 | 0.034 | 0.248 | 0.383 | 0.723 | 1.398 |
| pig 45 | 0.004 | 0.000 | 0.090 | 0.288 | 0.416 | 0.371 | 0.386 |
| pig 46 | 0.000 | 0.000 | 0.066 | 0.627 | 1.154 | 1.438 | 1.676 |
| mean | 0.001 | 0.000 | 0.042 | 0.380 | 0.773 | 1.089 | 1.354 |
| Means | 0 | 4 | 7 | 10 | 14 | 21 | 28 |

TABLE 6-continued

| ELISA Antibody Levels (S/P) | | | | | | | |
|---|---|---|---|---|---|---|---|
| | day 0 | day 4 | day 7 | day 10 | day 14 | day 21 | day 28 |
| P129-wt | 0.002 | 0.004 | 0.037 | 0.210 | 0.441 | 0.829 | 0.958 |
| P129-GG | 0.001 | 0.000 | 0.042 | 0.380 | 0.773 | 1.089 | 1.354 |

Serum neutralization titers were determined in both the T02 and T03 groups at 7, 14, 21 and 28 days post infection. The neutralizing titers were determined by TCID50 in 96 well plates in duplicate. In each well 200 pfu of wild type P129 virus in a volume of 100 µl was combined with 100 µl of a serial 2-fold dilution of sera (previously heat inactivated for 30 min at 56° C.). The mixture was incubated for 1 hr at 37 C, followed by infection of cells. The infected cells were incubated for 5 days and CPEs were determined. The data is presented below and shows that pigs infected with the mutant virus developed higher mean neutralizing titers than those infected with the wild type parent virus.

TABLE 7

| Neutralizing Titers During Four Weeks of Infection (duplicate values) | | | | |
|---|---|---|---|---|
| | Day 7 | Day 14 | Day 21 | Day 28 |
| P129-wt | | | | |
| Pig 28 | <2, <2 | <2, <2 | 4, 4 | 3.5 |
| Pig 30 | <2, <2 | 2, 8 | 2, 2 | 4 |
| Pig 35 | <2, <2 | 4, 4 | 8, 4 | 7.5 |
| Pig 40 | <2, <2 | 4, 4 | 2, 8 | 8 |
| Pig 43 | <2, <2 | 2, 4 | <2, 8 | 3.5 |
| Mean | <2 | 3.2 | 4.2 | 5.3 |
| P129-GG | | | | |
| Pig 33 | <2, <2 | 4, 8 | 8, 16 | 16 |
| Pig 36 | <2, <2 | 2, 2 | 16, 16 | 16 |
| Pig 38 | <2, <2 | 8, 4 | 8, 4 | 36 |
| Pig 45 | <2, <2 | 2, 2 | 4, 4 | 6 |
| Pig 46 | <2, <2 | 8, 8 | 16, 16 | 48 |
| Mean | <2 | 4.8 | 10.8 | 24.4 |

One of the hallmarks in PRRSV infection is the persistence of virus in tonsils. Therefore, tonsils were collected from all infected pigs and two mock-infected control pigs at the termination of the study (4 weeks post-infection) and examined for viral persistence by RT-PCR. The N gene was detectable by RT-PCR in all pigs infected with either GG virus or P129 virus, while tonsils from mock-infected pigs remained negative. This indicates that all infected pigs shed the virus at 4 weeks post-infection. To examine possible mutations in NLS of the N gene, PCR products from tonsils were sequenced.

In all five pigs, GG virus persisting in the tonsils was found to be mutated in the NLS-2 sequence by the introduction of an arginine at either position 43 or 44. Wild-type P129 virus from tonsils did not mutate and retained the wild-type NLS-2 sequence.

EXAMPLE 4

Reversion-Resistant Mutations of NLS-2

The P129-GG mutation described in Example 2 was created by changing six nucleotides. As seen in Example 3, this virus is capable of partial or full reversion and can regain the parental NLS-negative phenotype at a relatively high frequency due to random mutation and natural selection. Preferred embodiments of the invention, especially for vaccine purposes, would contain additional nucleotide substitutions and/or deletions, designed to minimize the probability of reversion, and to minimize the probability of other flanking residues mutating to basic residues such as lysine and arginine and thereby restoring a functional NLS motif in the region. Codons that require two or three separate nucleotide changes in order to mutate to codons encoding a basic residue are preferred over those that require only one change. Deletion mutations are very unlikely to revert, since a portion of the region has been removed. Alternative codons can be chosen for flanking amino acids, in order to reduce the chances of reacquiring a pat7, pat4, or other NLS motif by mutation. Examples of such "reversion resistant" mutations are shown in Table 6, and are intended to be representative rather than limiting. Given this information, other examples of reversion resistant mutations may be envisioned by one of ordinary skill in the art.

In Table 8, mutant virus P129-d43/44 is a deletion of amino acids 43 and 44. In addition, the serine codon at position 45 is changed from AGT to TCT to reduce the probability of it mutating to a lysine or arginine codon. Also, the asparagine codon at position 49 (AAC) is changed to a serine codon (TCC) for the same reason. Serine is found at position 49 in some naturally occurring field isolates, so should be well tolerated. A minimal pat 7 NLS motif (PGSKKKS) remains in this mutant, and may have partial NLS activity. Viruses with partial NLS activity are predicted to have phenotypes that are intermediate between wild type (parental) virus and complete NLS knockout mutants. Such viruses may be especially useful as vaccines.

Forward Primers (5'-3')

P129-d43/44 F (SEQ ID NO: 24)

GTCCAGAGGCAAGGGACCGGGATCTAA-GAAGAAATCCCCGGAG

P129-d43/44/46F (SEQ ID NO: 25)

GTCCAGAGGCAAGGGACCGGGATCTAA-GAAATCCCCGGAG

P129-d44/46/47F (SEQ ID NO: 26)

GCAAGGGACCGGGAAAGTCTAAATC-CCCGGAGAAGCCCC

P129-d46/47/48F (SEQ ID NO: 27)

GCAAGGGACCGGGAAAGAAATCTTC-CCCGGAGAAGCCCC

Reverse Primers (5'-3')

P129-d43/44 R (SEQ ID NO: 28)

CTCCGGGGATTTCTTCTTAGATCCCG-GTCCCTTGCCTCTGGAC

P129-d43/44/46R (SEQ ID NO: 29)

CTCCGGGGATTTCTTAGATCCCGGTC-CCTTGCCTCTGGAC

TABLE 8

Contemplated Deletion Mutants

| | | | | | | T Q N | N | D I N | M N | I Q N | E | K | | G | | | |
|---|---|---|---|---|---|---|---|---|---|---|---|---|---|---|---|---|---|
| V | R | | | E | | R | R | N | R | R | R | S | S | D | | | |
| 38 | 39 | 40 | 41 | 42 | 43 | 44 | 45 | 46 | 47 | 48 | 49 | 50 | 51 | 52 | 53 | | |
| G | K | G | P | G | K | K | S | K | K | K | N | P | E | K | P | wtP129 (SEQ ID NO:12) | |
| GGC | AAG | GGA | CCG | GGC | AAG | AAA | AGT | AAG | AAG | AAA | AAC | CCG | GAG | AAG | CCC | (SEQ ID NO:13) | |
| 38 | 39 | 40 | 41 | 42 | 43 | 44 | 45 | 46 | 47 | 48 | 49 | 50 | 51 | 52 | 53 | | |
| G | K | G | P | G | G | G | N | K | K | K | N | P | E | K | P | P129-GG SEQ ID NO:14) | |
| GGC | AAG | GGA | CCG | GGA | GGG | GGA | AAT | AAG | AAG | AAA | AAC | CCG | GAG | AAG | CCC | (SEQ ID NO:15) | |
| 38 | 39 | 40 | 41 | 42 | 43 | 44 | 45 | 46 | 47 | 48 | 49 | 50 | 51 | 52 | 53 | | |
| G | K | G | P | G | - | - | S | K | K | K | S | P | E | K | P | P129-d43/44 (SEQ ID NO: 16) | |
| GGC | AAG | GGA | CCG | GCG | --- | --- | TCT | AAG | AAG | AAA | TCC | CCG | GAG | AAD | CCC | (SEQ ID NO: 17) | |
| 38 | 39 | 40 | 41 | 42 | 43 | 44 | 45 | 46 | 47 | 48 | 49 | 50 | 51 | 52 | 53 | | |
| G | K | G | P | G | - | - | S | - | K | K | S | P | E | K | P | P129-d43/44/46 (SEQ ID NO: 18) | |
| GGC | AAG | GGA | CCG | GCG | --- | --- | TCT | --- | AAG | AAA | TCC | CCG | GAG | AAD | CCC | (SEQ ID NO: 19) | |
| 38 | 39 | 40 | 41 | 42 | 43 | 44 | 45 | 46 | 47 | 48 | 49 | 50 | 51 | 52 | 53 | | |
| G | K | G | P | G | K | - | S | - | - | K | S | P | E | K | P | P129-d44/46/47 (SEQ ID NO: 20) | |
| GGC | AAG | GGA | CCG | GCG | AAG | --- | TCT | --- | --- | AAA | TCC | CCG | GAG | AAD | CCC | (SEQ ID NO: 21) | |
| 38 | 39 | 40 | 41 | 42 | 43 | 44 | 45 | 46 | 47 | 48 | 49 | 50 | 51 | 52 | 53 | | |
| G | K | G | P | G | K | K | S | - | - | - | S | P | E | K | P | P129-d46/47/48 (SEQ ID NO: 22) | |
| GGC | AAG | GGA | CCG | GCG | AAG | AAA | TCT | --- | --- | --- | TCC | CCG | GAG | AAD | CCC | (SEQ ID NO: 23) | |

The letters in bold at the top above are alternative residues that are found in at least one NA PRRS virus.
The two underlined segments form a 5-base stem that may be important for negative strand synthesis.
4 and 5 residue deletions are also contemplated The other three mutants shown in Table 8 (P129-d43/44/46, P129-d44/46/47, and P129-d46/47/48) are deletions of three amino acids, and also have the codon changes at positions 45 and 49 discussed above. These mutations lack an NLS motif and are predicted to have a complete knockout of NLS activity. These viruses are anticipated to be attenuated in pigs and especially useful as vaccines.

The forward and reverse primers for the mutations described in Table 8 are as follows:

P129-d44/46/47R (SEQ ID NO: 30)

GGGGCTTCTCCGGGGATTTAGACTTTC-CCGGTCCCTTGC

P129-d46/47/48R (SEQ ID NO: 31)

GGGGCTTCTCCGGGGAAGATTTCTTTC-CCGGTCCCTTGC

The descriptions and examples above demonstrate that the NLS-2 regions is not required for virus multiplication but is an important virulence factor for PRRSV, as demonstrated by the fact that the only virus persisting in tonsils has mutated. We also demonstrate that the NLS in the PRRSV N protein is positively correlated with higher neutralizing antibodies and higher ELISA titers. We thus have established that mutations eliminating the NLS-2 sequence motif result in an attenuated strain of PRRSV.

NUMBERED DESCRIPTION OF THE INVENTION

1. A composition comprising a PRRS infectious agent selected from the group consisting of: a.) a genetically modified PRRS virus comprising an N protein which has been modified in at least one conserved region selected from the group consisting of the NLS-2 region, NoLS region and the NES region such that the conserved region has been eliminated, and wherein the genetically modified PRRS virus is attenuated; b.) an infectious RNA molecule encoding the genetically modified PRRS virus of a.); and c.) an isolated polynucleotide molecule comprising a DNA sequence encoding the infectious RNA molecule of b.). 2. The composition of claim 1 which has been further modified to result in the elimination of the conserved NLS-1 region. 3. The composition of claim 1 wherein the conserved region has been eliminated by the introduction of a non-conservative amino acid substitution. 4. The composition of claim 1 or 2 wherein the conserved region has been at least partially deleted. 5. The composition of claim 1 wherein the conserved region is the NoLS region. 6. The composition of claim 1 wherein the conserved region is the NLS-2 region. 7. The composition of claim 1 wherein the conserved region is the NES region. 8. The composition of claim 1 wherein the PRRS virus is a North American PRRS virus. 9. The composition of claim 1 wherein the PRRS virus is a European PRRS virus. 10. The composition of claim 8 wherein the conserved region is the NLS-2 region. 11. The composition of claim 10 wherein residues 42 and 43 of the N protein are glycines. 12. The composition of claim 10 wherein residues 42 and 43 of the N protein are glycine and residue 44 is an asparagine. 13. The composition of claim 10 wherein the NLS-2 region has been at least partially deleted. 14. The composition of claim 13 wherein at least one of residues 43 through 48 of the N protein have been deleted. 15. The composition of claim 14 wherein both residues 43 and 44 of the N protein have been deleted. 16. The composition of claim 14 wherein residues 43, 44, and 46 of the N protein have been deleted. The composition of claim 14 wherein residues 44, 46, and 47 of the N protein have been deleted. 17. The composition of claim 14 wherein residues 46, 47, and 48 of the N protein have been deleted. 18. The composition of claim 1 that contain additional nucleotide mutation, substitutions and/or deletions, designed to minimize the probability of reversion.

19. A vaccine for protecting a porcine animal from infection by a PRRS virus comprising the composition of any of claim 1 in an amount effective to produce immunoprotection against infection by a PRRS virus; and a carrier acceptable for veterinary use. 20. A method for protecting a porcine animal from infection by a PRRS virus, which comprises vaccinating the animal with an amount of the vaccine of claim 19 that is effective to produce immunoprotection against infection by a PRRS virus. 21. A transfected host cell comprising a composition according to any of claim 1.

22. A method for making a genetically modified and attenuated PRRS virus, which method comprises: a.) mutating a DNA sequence encoding an infectious RNA molecule which encodes a PRRS virus, to produce a genetically modified PRRS virus comprising an N protein which has been modified in an at least one conserved region selected from the group consisting of the NLS-2 region, NoLS region and the NES region such that the conserved region has been eliminated; b.) introducing the genetically modified PRRS virus into a host cell capable of supporting PRRS replication. 23. A method of claim 22 wherein the genetically modified PRRS virus is a North American PRRS virus. 24. A method of claim 22 wherein the genetically modified PRRS virus is a European PRRS virus. 25. The method of claim 22 wherein the host cell capable of supporting PRRS replication is a MARC-145 cell. 26. The method of claim 22 wherein the host cell capable of supporting PRRS replication is comprised within a live porcine animal.

What is claimed is:

1. A composition comprising a PRRS virus infectious agent selected from the group consisting of:
   a) an isolated genetically modified PRRS virus, comprising an N protein which has been modified in the NLS-2 region thereof compared to wild-type sequence, wherein the modification to the NLS-2 region of the N protein is in the pat8 or pat7 motif thereof and wherein the genetically modified PRRS virus is attenuated as a result of said modification to the N protein;
   b) an infectious RNA molecule encoding the genetically modified PRRS virus of a); and
   c) an isolated polynucleotide molecule comprising a DNA sequence encoding the infectious RNA molecule of b).

2. A composition comprising a PRRS virus infectious agent selected from the group consisting of:
   a) an isolated genetically modified PRRS virus, comprising an N protein which has been modified in the NLS-1 region thereof compared to wild-type sequence, and wherein the genetically modified PRRS virus is attenuated as a result of said modification to the N protein;
   b) an infectious RNA molecule encoding the genetically modified PRRS virus of a); and
   c) an isolated polynucleotide molecule comprising a DNA sequence encoding the infectious RNA molecule of b).

3. The composition of claim 1, wherein a modification of the NLS-2 region of the N protein is a non-conservative amino acid substitution or an amino acid deletion.

4. The composition of claim 3, wherein residues 42 and 43 of the N protein are glycines.

5. The composition of claim 3 wherein residues 42 and 43 of the N protein are glycine and residue 44 is an asparagine.

6. The composition of claim 3 wherein at least one of residues 43 through 48 of the N protein have been deleted.

7. The composition of claim 3 wherein both residues 43 and 44 of the N protein have been deleted.

8. The composition of claim 3 wherein residues 43, 44 and 46 of the N protein have been deleted.

9. The composition of claim 3 wherein residues 44, 46 and 47 of the N protein have been deleted.

10. The composition of claim 3 wherein residues 46, 47, and 48 of the N protein have been deleted.

11. The composition of claim 3, wherein although a particular further amino acid in the NLS-2 region is not changed relative to wild type, the codon for said amino acid is changed to inhibit subsequent mutation of said codon to one encoding for a basic amino acid.

12. The composition of claim 3, wherein the codon for any amino acid in said NLS-2 region has been altered to inhibit subsequent mutation of said codon to one encoding for a basic amino acid.

13. The composition of claim 12, wherein serine 45 is encoded by TCT and not AGT.

14. The composition of claim 12, wherein asparagine 49 encoded from AAC is replaced by serine encoded from TCC.

15. The composition of claim 1 wherein the encoding sequence of the NLS-2 region of the N protein of said PRRS virus further comprises an additional nucleotide mutation, substitution, and/or deletion, designed to minimize the probability of reversion.

16. A composition comprising a North American PRRS virus infectious agent selected from the group consisting of:
   a) an isolated genetically modified PRRS virus, comprising an N protein which has been modified in the NLS-2 region thereof compared to wild-type sequence, wherein the modification to the NLS-2 region of the N protein is in the pat8 or pat7 motif thereof, and wherein the genetically modified PRRS virus is attenuated as a result of said modification to the N protein;
   b) an infectious RNA molecule encoding the genetically modified PRRS virus of a); and
   c) an isolated polynucleotide molecule comprising a DNA sequence encoding the infectious RNA molecule of b).

17. A vaccine for protecting a porcine animal from infection by a PRRS virus comprising the composition of claim 1, in an amount effective to produce immunoprotection against infection by a PRRS virus; and a carrier acceptable for veterinary use.

18. A vaccine for protecting a porcine animal from infection by a PRRS virus comprising the composition of claim 16, in an amount effective to produce immunoprotection against infection by a PRRS virus; and a carrier acceptable for veterinary use.

19. A vaccine for protecting a porcine animal from infection by a PRRS virus comprising the composition of claim 2, in an amount effective to produce immuno-protection against infection by a PRRS virus; and a carrier acceptable for veterinary use.

* * * * *

UNITED STATES PATENT AND TRADEMARK OFFICE
CERTIFICATE OF CORRECTION

PATENT NO. : 7,544,362 B1
APPLICATION NO. : 11/359334
DATED : June 9, 2009
INVENTOR(S) : Yoo et al.

It is certified that error appears in the above-identified patent and that said Letters Patent is hereby corrected as shown below:

On the title page,

[*] Notice:   Subject to any disclaimer, the term of this patent is extended or adjusted under 35 USC 154(b) by 100 days Delete the phrase "by 100 days" and insert -- by 207 days --

Signed and Sealed this

Twenty-seventh Day of July, 2010

David J. Kappos
*Director of the United States Patent and Trademark Office*

SEQUENCE LISTING

```
<160> NUMBER OF SEQ ID NOS: 31

<210> SEQ ID NO 1
<211> LENGTH: 8
<212> TYPE: PRT
<213> ORGANISM: Porcine reproductive and respiratory syndrome virus

<400> SEQUENCE: 1

Pro Gly Lys Lys Asn Lys Lys Lys
1               5

<210> SEQ ID NO 2
<211> LENGTH: 32
<212> TYPE: PRT
<213> ORGANISM: Porcine reproductive and respiratory syndrome virus

<400> SEQUENCE: 2

Pro Gly Lys Lys Asn Lys Lys Lys Asn Pro Glu Lys Pro His Phe Pro
1               5                   10                  15

Leu Ala Thr Glu Asp Asp Val Arg His His Phe Thr Pro Ser Glu Arg
            20                  25                  30
```

```
<210> SEQ ID NO 3
<211> LENGTH: 33
<212> TYPE: PRT
<213> ORGANISM: Porcine reproductive and respiratory syndrome virus

<400> SEQUENCE: 3

Pro Arg Gly Gly Gln Ala Lys Lys Lys Pro Glu Lys Pro His Phe
1               5                   10                  15

Pro Leu Ala Ala Glu Asp Asp Ile Arg His His Leu Thr Gln Thr Glu
            20                  25                  30

Arg

<210> SEQ ID NO 4
<211> LENGTH: 12
<212> TYPE: PRT
<213> ORGANISM: Porcine reproductive and respiratory syndrome virus

<400> SEQUENCE: 4

Leu Pro Thr His His Thr Val Arg Leu Ile Arg Val
1               5                   10

<210> SEQ ID NO 5
<211> LENGTH: 12
<212> TYPE: PRT
<213> ORGANISM: Porcine reproductive and respiratory syndrome virus

<400> SEQUENCE: 5

Leu Pro Val Ala His Thr Val Arg Leu Ile Arg Val
1               5                   10

<210> SEQ ID NO 6
<211> LENGTH: 123
<212> TYPE: PRT
<213> ORGANISM: Porcine reproductive and respiratory syndrome virus

<400> SEQUENCE: 6

Met Pro Asn Asn Asn Gly Lys Gln Gln Lys Lys Lys Lys Gly Asn Gly
1               5                   10                  15

Gln Pro Val Asn Gln Leu Cys Gln Met Leu Gly Lys Ile Ile Ala Gln
            20                  25                  30

Gln Asn Gln Ser Arg Gly Lys Gly Pro Gly Lys Lys Ser Lys Lys Lys
        35                  40                  45

Asn Pro Glu Lys Pro His Phe Pro Leu Ala Thr Glu Asp Asp Val Arg
    50                  55                  60

His His Phe Thr Pro Gly Glu Arg Gln Leu Cys Leu Ser Ser Ile Gln
65                  70                  75                  80

Thr Ala Phe Asn Gln Gly Ala Gly Thr Cys Thr Leu Ser Asp Ser Gly
                85                  90                  95

Arg Ile Ser Tyr Thr Val Glu Phe Ser Leu Pro Thr His His Thr Val
            100                 105                 110

Arg Leu Ile Arg Val Thr Ala Ser Pro Ser Ala
        115                 120

<210> SEQ ID NO 7
<211> LENGTH: 369
<212> TYPE: DNA
<213> ORGANISM: Porcine reproductive and respiratory syndrome virus

<400> SEQUENCE: 7
```

-continued

```
atgccaaata caacggcaa gcagcaaaag aaaaagaagg ggaatggcca gccagtcaat      60
cagctgtgcc agatgctggg taaaatcatc gcccagcaaa accagtccag aggcaaggga    120
ccgggcaaga aaagtaagaa gaaaaacccg gagaagcccc attttcctct agcgaccgaa    180
gatgacgtca ggcatcactt caccctggt gagcggcaat tgtgtctgtc gtcgatccag    240
actgccttta accagggcgc tggaacttgt accctgtcag attcaggag gataagttac    300 actgtggagt ttagttttgcc gacgcatcat actgtgcgcc tgatccgcgt cacagcatca    360
ccctcagca                                                            369
```

<210> SEQ ID NO 8
<211> LENGTH: 27
<212> TYPE: DNA
<213> ORGANISM: Porcine reproductive and respiratory syndrome virus

<400> SEQUENCE: 8

```
actcagtcta agtgctggaa agttatg                                         27
```

<210> SEQ ID NO 9
<211> LENGTH: 27
<212> TYPE: DNA
<213> ORGANISM: Porcine reproductive and respiratory syndrome virus

<400> SEQUENCE: 9

```
atcttatcat gtctggatcc ccgcggc                                         27
```

<210> SEQ ID NO 10
<211> LENGTH: 36
<212> TYPE: DNA
<213> ORGANISM: Porcine reproductive and respiratory syndrome virus

<400> SEQUENCE: 10

```
ggcaagggac cgggagggggg aaataagaag aaaaac                              36
```

<210> SEQ ID NO 11
<211> LENGTH: 36
<212> TYPE: DNA
<213> ORGANISM: Porcine reproductive and respiratory syndrome virus

<400> SEQUENCE: 11

```
gttttttcttc ttatttcccc ctcccggtcc cttgcc                              36
```

<210> SEQ ID NO 12
<211> LENGTH: 16
<212> TYPE: PRT
<213> ORGANISM: Porcine reproductive and respiratory syndrome virus

<400> SEQUENCE: 12

Gly Lys Gly Pro Gly Lys Lys Ser Lys Lys Asn Pro Glu Lys Pro
1               5                   10                  15

<210> SEQ ID NO 13
<211> LENGTH: 48
<212> TYPE: DNA
<213> ORGANISM: Porcine reproductive and respiratory syndrome virus

<400> SEQUENCE: 13

```
ggcaagggac cgggcaagaa aagtaagaag aaaaacccgg agaagccc                  48
```

<210> SEQ ID NO 14
<211> LENGTH: 16
<212> TYPE: PRT

-continued

<213> ORGANISM: Porcine reproductive and respiratory syndrome virus

<400> SEQUENCE: 14

Gly Lys Gly Pro Gly Gly Gly Asn Lys Lys Asn Pro Glu Lys Pro
1               5                   10                  15

<210> SEQ ID NO 15
<211> LENGTH: 48
<212> TYPE: DNA
<213> ORGANISM: Porcine reproductive and respiratory syndrome virus

<400> SEQUENCE: 15
ggcaagggac cgggaggggg aaataagaag aaaaacccgg agaagccc                48

<210> SEQ ID NO 16
<211> LENGTH: 14
<212> TYPE: PRT
<213> ORGANISM: Porcine reproductive and respiratory syndrome virus

<400> SEQUENCE: 16

Gly Lys Gly Pro Gly Ser Lys Lys Lys Ser Pro Glu Lys Pro
1               5                   10

<210> SEQ ID NO 17
<211> LENGTH: 42
<212> TYPE: DNA
<213> ORGANISM: Porcine reproductive and respiratory syndrome virus

<400> SEQUENCE: 17
ggcaagggac cgggctctaa gaagaaatcc ccggagaagc cc                      42

<210> SEQ ID NO 18
<211> LENGTH: 13
<212> TYPE: PRT
<213> ORGANISM: Porcine reproductive and respiratory syndrome virus

<400> SEQUENCE: 18

Gly Lys Gly Pro Gly Ser Lys Lys Ser Pro Glu Lys Pro
1               5                   10

<210> SEQ ID NO 19
<211> LENGTH: 39
<212> TYPE: DNA
<213> ORGANISM: Porcine reproductive and respiratory syndrome virus

<400> SEQUENCE: 19
ggcaagggac cgggctctaa gaaatccccg gagaagccc                          39

<210> SEQ ID NO 20
<211> LENGTH: 13
<212> TYPE: PRT
<213> ORGANISM: Porcine reproductive and respiratory syndrome virus

<400> SEQUENCE: 20

Gly Lys Gly Pro Gly Lys Ser Lys Ser Pro Glu Lys Pro
1               5                   10

<210> SEQ ID NO 21
<211> LENGTH: 39
<212> TYPE: DNA
<213> ORGANISM: Porcine reproductive and respiratory syndrome virus

<400> SEQUENCE: 21
ggcaagggac cgggcaagtc taaatccccg gagaagccc                          39

<210> SEQ ID NO 22
<211> LENGTH: 13
<212> TYPE: PRT
<213> ORGANISM: Porcine reproductive and respiratory syndrome virus

<400> SEQUENCE: 22

Gly Lys Gly Pro Gly Lys Lys Ser Ser Pro Glu Lys Pro
1               5                   10

<210> SEQ ID NO 23
<211> LENGTH: 39
<212> TYPE: DNA
<213> ORGANISM: Porcine reproductive and respiratory syndrome virus

<400> SEQUENCE: 23
ggcaagggac cgggcaagaa atcttccccg gagaagccc                              39

<210> SEQ ID NO 24
<211> LENGTH: 43
<212> TYPE: DNA
<213> ORGANISM: Porcine reproductive and respiratory syndrome virus

<400> SEQUENCE: 24
gtccagaggc aagggaccgg gatctaagaa gaaatccccg gag                         43

<210> SEQ ID NO 25
<211> LENGTH: 40
<212> TYPE: DNA
<213> ORGANISM: Porcine reproductive and respiratory syndrome virus

<400> SEQUENCE: 25
gtccagaggc aagggaccgg gatctaagaa atccccggag                             40

<210> SEQ ID NO 26
<211> LENGTH: 39
<212> TYPE: DNA
<213> ORGANISM: Porcine reproductive and respiratory syndrome virus

<400> SEQUENCE: 26
gcaagggacc gggaaagtct aaatccccgg agaagcccc                              39

<210> SEQ ID NO 27
<211> LENGTH: 39
<212> TYPE: DNA
<213> ORGANISM: Porcine reproductive and respiratory syndrome virus

<400> SEQUENCE: 27
gcaagggacc gggaaagaaa tcttccccgg agaagcccc                              39

<210> SEQ ID NO 28
<211> LENGTH: 43
<212> TYPE: DNA
<213> ORGANISM: Porcine reproductive and respiratory syndrome virus

<400> SEQUENCE: 28
ctccggggat ttcttcttag atcccggtcc cttgcctctg gac                         43

<210> SEQ ID NO 29
<211> LENGTH: 40
<212> TYPE: DNA
<213> ORGANISM: Porcine reproductive and respiratory syndrome virus

<400> SEQUENCE: 29

-continued

```
<210> SEQ ID NO 30
<211> LENGTH: 39
<212> TYPE: DNA
<213> ORGANISM: Porcine reproductive and respiratory syndrome virus

<400> SEQUENCE: 30
ggggcttctc cggggattta gactttcccg gtcccttgc                              39

<210> SEQ ID NO 31
<211> LENGTH: 39
<212> TYPE: DNA
<213> ORGANISM: Porcine reproductive and respiratory syndrome virus

<400> SEQUENCE: 31
ggggcttctc cggggaagat ttctttcccg gtcccttgc                              39
```